US005486611A

United States Patent [19]
Lin et al.

[11] Patent Number: 5,486,611
[45] Date of Patent: Jan. 23, 1996

[54] CARBOXAMIDO-(1,2N)-CARBOCYCLIC-2-AMINOTETRALIN DERIVATIVES

[75] Inventors: Chiu-Hong Lin, Portage, Mich.;
Susanne R. Haadsma-Svensson,
Gothenburg, Sweden; Robert B. McCall, Kalamazoo, Mich.; Arthur G. Romero, Kalamazoo, Mich.; William H. Darlington, Kalamazoo, Mich.;
Michael D. Ennis, Portage, Mich.

[73] Assignee: The Upjohn Company, Kalamazoo, Mich.

[21] Appl. No.: 144,851

[22] Filed: Oct. 28, 1993

Related U.S. Application Data

[63] Continuation-in-part of PCT/US92/03871, filed May 13, 1992, which is a continuation-in-part of both PCT/US92/01651, filed Mar. 11, 1991, and continuation of Ser. No. 702,814, May 20, 1991, abandoned, and a continuation-in-part of Ser. No. 803,287, Dec. 4, 1991, which is a continuation of PCT/US90/03551, filed Jun. 27, 1990, abandoned, which is a continuation-in-part of Ser. No. 379,526, Jul. 13, 1989, abandoned.

[51] Int. Cl.$^6$ .......................... C07D 209/60; A61K 31/40
[52] U.S. Cl. ........................ 546/62; 546/101; 548/421; 548/427
[58] Field of Search ...................... 546/62, 101; 548/427, 548/421

[56] References Cited

U.S. PATENT DOCUMENTS

| | | | |
|---|---|---|---|
| 3,890,347 | 6/1975 | Middlemiss et al. | 548/427 |
| 4,234,731 | 11/1980 | Kavadias | 548/427 |
| 4,622,405 | 11/1986 | De Bernerdis et al. | |

FOREIGN PATENT DOCUMENTS

| | | |
|---|---|---|
| 059553 | 3/1982 | European Pat. Off. . |
| 127597 | 12/1984 | European Pat. Off. . |
| 270947 | 6/1988 | European Pat. Off. . |
| 272534 | 6/1988 | European Pat. Off. . |
| 0548664 | 6/1994 | European Pat. Off. . |
| 2146503 | 3/1973 | France . |
| 2044172 | 5/1971 | Germany . |
| 12803582 | 8/1979 | Germany . |
| 1377356 | 12/1974 | United Kingdom . |
| 2138815 | 10/1984 | United Kingdom . |
| 9015047 | 12/1990 | WIPO . |
| 9100856 | 1/1991 | WIPO . |
| 9113872 | 9/1991 | WIPO . |

OTHER PUBLICATIONS

Chemical Abstracts vol. 119:8696 (1993).
D. Ghosh, et al., Abstract No. 90, 203rd meeting of the American Chemical Society, Apr. 5–10, 1992.
Chemical Abstract 86, 456 (1977) abstract 5285g, "Studies on analgesic-narcotic antagonists: synthesis of N-substituted 1,2,3,4,4a,5,6,10b-octahydrobenzo[f] quinolines".
L. E. Arvidsson et al, J. Med. Chem 24, 921–923 (1981), "8-Hydroxy-2-(di-n-propylamino)tetralin, a New Centrally Acting 5-Hydroxytryptamine Receptor Agonist".

L. E. Arvidsson et al, J. Med Chem 27, 45 (1984), "8-Hydroxy-2-(alkylamino)tetralins and Related Compounds as Central 5-Hydroxytryptamine Receptor Agonists".
L. E. Arvidsson et al, J. Med Chem 30, 2105 (1987), "(+)-cis-8-Hydroxy-1-methyl-2-(di-n-propylamino)tetralin: A Potent and Highly Stereoselective 5-Hydroxytryptamine Receptor Agonist".
John D. McDermed et al, J. Med Chem 18, 362 (1975), "Synthesis and Pharmacology of Some 2-Aminotetralins. Dopamine Receptor Agonists".
John D. McDermed et al, J. Med Chem 19, 547 (1976), "Synthesis and Dopaminergic Activity of (±)-,(+)-, and (−)-2-Dipropylamino-5-hydroxy-1,2,3, 4-tetrahydronaphthalene".
David B. Rusterholz et al, J. Med Chem 19, 99 (1976), "Ergoline Congeners as Potential Inhibitors of Prolactin Release".
D. E. Ames et al, J. Chem Soc, 2636 (1965), "The Synthesis of Alkoxy-1,2,3,4-tetrahydronaphthalene Derivatives. Part I. 2-Amino-, Alkylamino-, and Dialkylamino-derivatives".
Anthony T. Dren et al, J. Pharm Sciences 67, 880–82 (1978), "Local Anesthetic Activity and Acute Toxicity of N-Substituted 1,2,3,4-Tetrahydro-1- and 2-naphthylamines".
S. Hjorth et al, J. Neural Transm 55, 169–188 (1982), "8-Hydroxy-2-(Di-n-Propylamino)Tetralin, OH-DPAT, a Potent and Selective Simplified Ergot Congener with Central 5-HT-Receptor Stimulating Activity".
C. Mellin et al, J. Med Chem 31, 1130 (1988), "Central Dopaminergic and 5-Hydroxytryptaminergic Effects of C3-Methylated Derivatives of 8-Hydroxy-2-(di-n-propylamino)tetralin".
J. M. Cossery et al, Euro J. Pharm 140, 143–155 (1987), "The selective labelling of central 5-HT$_{1A}$ receptor binding sites by [$^3$H]5-methoxy-3-(di-n-propylamino)chroman".
L. E. Arvidsson et al, J. Med Chem 27, 45 [1983] (1984), "8-Hydroxy-2-(alkylamino)tetralins and Related Compounds as Central 5-Hydroxytryptamine Receptor Agonists".

(List continued on next page.)

Primary Examiner—Nicholas Rizzo
Attorney, Agent, or Firm—Sidney B. Williams; Donald L. Corneglio

[57] ABSTRACT

This invention is therapeutically useful tetralins and pharmaceutically acceptable acid addition salts thereof of the formula I:

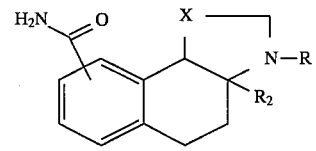

wherein X is —(CH$_2$)$_n$— or —C(R$_1$)(H)—; R is C$_1$–C$_8$ alkyl; and R$_1$ and R$_2$ are the same or different and are selected from the group consisting of hydrogen, C$_1$–C$_8$ alkyl, C$_2$–C$_8$ alkenyl, C$_2$–C$_8$ alkynyl, aryl and benzyl.

These compounds are useful to treat central nervous system disorders and are unexpectedly resistant to metabolism by the liver and have superior oral plasma bioavailability.

18 Claims, No Drawings

OTHER PUBLICATIONS

J. G. Cannon et al, J. Med Chem 29, 2529–2534 (1986), "p–Dimethoxy–Substituted trans–Octahydrobenzo[f]–and –[g]quinolines: Synthesis and Assessment of Dopaminergic Agonist Effects".

J. G. Cannon et al, J. Med Chem 29, 2016–2020 (1986), "Assessment of a Potential Dopaminergic Prodrug Moiety in Several Ring Systems".

J. G. Cannon et al, J. Med Chem 23, 1–4 (1980), "Congeners of the β Conformer of Dopamine Derived from cis– and trans–Octahydrobenzo[f]quinoline and trans–Octahydrobenzo[g]quinoline".

J. G. Cannon et al, J. Med Chem 22, 341–347 (1979), "Rigid Congeners of Dopamine Based on Octahydrobenzo[f]quinoline: Peripheral and Central Effects".

H. Wikstrom, et al, J. Med Chem 30, 1567–1573 (1987), "Resolved cis–10–Hydroxy–4–n–propyl–1,2,3,4,4a,5,6,10b–octahydrobenzo[f]quinoline: Central Serotonin Stimulating Properties".

H. Wikstrom, et al, J. Med Chem 25, 925–931 (1982), "Monophenolic Octahydrobenzo[f]quinolines: Central Dopamine– and Serotonin–Receptor Stimulating Activity".

H. Wikstrom, et al, J. Med Chem 30, 2169–2174 (1987), "N–Substituted 1,2,3,4,4a,5,6,10b–Octahydrobenzo[f]quinolines and 3–Phenylpiperidines: Effects on Central Dopamine and σ Receptors".

CARBOXAMIDO-(1,2N)-CARBOCYCLIC-2-AMINOTETRALIN DERIVATIVES

CROSS REFERENCE TO RELATED APPLICATIONS

The present application is a continuation-in-part of PCT/US92/03871, filed May 13, 1992 which was a continuation-in-part of both: PCT/US92/01651, filed Mar. 11, 1992, which was a continuation of U.S. Ser. No. 07/702,814, filed May 20, 1991, abandoned; and U.S. Ser. No. 07/803,297 filed Dec. 4, 1991, abandoned, which was a continuation of PCT/US90/03551, filed Jun. 27, 1990, which was a continuation-in-part of U.S. Ser. No. 07/379,526, filed Jul. 13, 1989, abandoned.

FIELD OF THE INVENTION

The present invention is related to new carboxamido-(1,2N)-carbocyclic-2-amino-1,2,3,4-tetrahydro-2-naphthylene derivatives, to processes for preparing such compounds, pharmaceutical preparation of such compounds and the use of such compounds in manufacture of a pharmaceutical preparation.

BACKGROUND OF THE INVENTION

Psychiatric diseases are thought to be due to dysfunctions in monoaminergic neuronal systems, particularly those involving serotonin (5-HT) and dopamine (DA).

Anxiety is associated with increased activity in 5-HT systems. In animals where 5-HT has been depleted, benzodiazepine anxiolytics are not active in anti-anxiety assays that they otherwise are effective in. Serotonin neurons have autoreceptors that, when activated by agonists, depress firing rates of 5-HT cells. These receptors are of the 5-HT$_{1A}$ subtype. Because they depress 5-HT neuronal activity, it can be expected that 5-HT$_{1A}$ agonists will be an effective anxiolytic. Clinically, 5-HT$_{1A}$ agonists have demonstrated anxiolytic properties. The drug Buspirone, is the only currently available marketed 5-HT$_{1A}$ agonist having anxiolytic activity. This compound antagonizes dopamine receptors at the same dose it stimulates 5-HT$_{1A}$ receptors. A similar drug, Gepirone, also has dopamine antagonist properties. These dopamine antagonist properties reduce the clinical utility of these compounds because long term treatment with dopamine antagonists can produce tardive dyskinesia.

Depression is a psychiatric condition thought to be associated with decreased 5-HT release. Most anti-depressants potentiate the effects of 5-HT by blocking the termination of activity through re-uptake into nerve terminals. Since some 5-HT$_{1A}$ receptors are activated postsynaptically by 5-HT, 5-HT$_{1A}$ agonists may also be anti-depressants. Since the postsynaptic 5-HT$_{1A}$ receptor may be less sensitive than the autoreceptor, high doses of 5-HT$_{1A}$ agonists, particularly very effective ones (i.e., those causing greater stimulation of the 5-HT$_{1A}$ receptor, a parameter referred to as "efficacy"), can be expected to be effective anti-depressants. Gepirone has already been demonstrated to have ameliorative effects on some depressive endpoints in some patients.

Serotonin is also involved in the regulation of feeding and sexual behavior and in cardiovascular regulation. Thus, 5-HT$_{1A}$ agonists may be useful in treating overeating and sexual dysfunction. These compounds have been shown to alter feeding and sexual behavior in animals. 5-HT$_{1A}$ agonists are also known to depress sympathetic nerve discharge and thus lower blood pressure. Thus, they may be useful in treating hypertension, congestive heart failure (by reducing cardiovascular afterload) and cardiac arrythmias (by removing sympathetic drive to the heart).

The compounds of the present invention have a variety of effects at the 5-HT$_{1A}$ receptor, and offer a variety of utilities associated with those activities.

The search for new CNS active compounds is focused on finding compounds with selective 5-HT$_{1A}$ receptor agonist effects without detrimentally influencing central dopamine receptors. Compounds resistant to liver metabolism would be expected to have a greater oral bioavailability and therefore a significant therapeutic advantage over rapidly metabolized compounds.

INFORMATION DISCLOSURE STATEMENT

Ghosh, D., et al, describes Synthesis and Evaluation of Hexahydro-3H-Benz[e]indoles at D1 and D2 Receptors, Abstract #90 at the 203rd Meeting of the American Chemical Society, Apr. 5–10, 1992.

Arvidsson, L.-E., et at., J. Med. Chem., 24, 921 (1981), describes hydroxy-2-aminoletralins where the amine is substituted with one n-propyl, one benzyl or two n-propyl substituents. The 5-, 6-, and 7-hydroxy compounds are described as active central dopamine-receptor agonists and the 8-hydroxy compound is described as a central 5-HT receptor agonist devoid of dopamine receptor stimulating activity.

Arvidsson, L.-E., et at., J. Med. Chem., 27, 45 (1984), describes 2-aminotetralins where the amine is substituted with one or two methyl, ethyl, n-propyl, i-propyl, n-butyl, or benzyl substituents. The 2-piperidinyltetralin is also described. Several of these compounds were found to be potent 5-HT agonists devoid of dopamine-mimetic effects.

Arvidsson, L.-E., et at., J. Med. Chem., 30, 2105 (1987), describes 8-hydroxy-1-methyl-2-(di-n-propylamino)tetralins. These compounds were 5-HT receptor agonists.

The Arvidsson. L.-E., et al 8-hydroxy and 8-methoxy tetratin compounds are also disclosed in Derwent documents 00389J/47, 94981D/51 and 045535J.48.

McDermed, et at., J. Med. Chem., 18, 362 (1975) describes 5,6-dihydroxy-2-aminotetralins. In addition, the 5,8 and 7,8 disubstituted compounds are also disclosed. The amine can be a mono or di substituted with simple alkyl groups, benzyl groups alkylalkoxy groups or the amine can be a 5 or 6 membered hydrocarbon or heterocyclic amine. These compounds are indicated to have dopaminergic properties although certain compounds are reported to be inactive.

McDermed, et at., J. Med. Chem., 19, 547 (1976) describes 5-, 6-, or 7-hydroxy-2-dipropylaminotetralins. These compounds are described as dopaminergic compounds.

Rusterholz, et al., J. Med. Chem., 19, 99 (1976) describes 5,8 disubstituted-2-aminotetralins with the amine being substituted with hydrogen, methyl, or cyanopropyl groups. Some of these compounds are potent prolactin inhibitors and believed to be dopamine agonists.

Ames, et at., J. Chem. Soc. 2636 (1965) describes the preparation of a large number of compounds, where the aromatic ring is substituted by methoxy, ethoxy, n- or iso-propoxy, or n-, sec- or tert-butoxy group in the 5 or 8 position and the amine is substituted by hydrogen or alkyl groups having 114 carbon atoms. The compounds are indicated to be prepared for pharmacological testing. However, no utility or pharmacological activity is yet known for the compounds just mentioned.

German Patent DE-A1-2 803 582 describes 2-aminotetralins where the aromatic ring is substituted on the 5,6,7 or 8 position a group $R_1$, where $R_1$ is hydrogen, alkanoyl having 1 to 20 carbon atoms or a group $-CO-(CH_2)_n-R_7$, n is a number 0 to 5, $R_7$ is a phenyl group with substituents as defined further, $R_2$ is hydrogen, hydroxy, halogen or alkylsulfonylamino, $R_3$ is hydrogen, $R_4$ is hydrogen, $CH_2OH$, $CH_2O-CO-R_8$ or $CH_2O-CO-(CH_2)_n-R_7$ with further definition and $R_5$ and $R_6$ are hydrogen, alkyl or aryl or aralkyl groups further defined or $R_5$ and $R_6$ are together an alkylene with 4 to 6 carbon atoms. The compounds are disclosed as having pharmacodynamic activity in particular a stimulating effect on alpha-and beta-adrenoceptors and dopamine receptors. Among the compounds described are compounds having the group $R_{10}$ in the 8 position and having $R_2$ or $R_4$ other than hydrogen.

Great Britain Patent 1,377,356 describes 2-aminotetralins where the aromatic ring is substituted on the 5,6,7 or 8 position by $R_1$, where $R_1$ is hydrogen or methyl, the aliphatic ring is substituted by $R_2$, where $R_2$ is alkyl having 1–6 carbon atoms, and the amine is substituted by R3, where $R_3$ is hydrogen or alkyl having 1–6 carbon atoms are described. Such compounds are stated to possess analgesic activity. 1,1-Dimethyl-2-(N,N-dimethylamino)-7-hydroxytetralin is mentioned as one example of a compound covered by the patent. This compound is also described in Chem. Ab., 79: 146294b as having analgesic and intestinal movement accelerating actions. J. Pharm. Sci., 67, 880–82 (1978) describes the compound 1-methyl-2-(cyclopropylamino)-5-methoxytetralin and indicates the compound possess local anesthetic activity. Derwent documents 58,247B/32, 40 378A/23, 83-729388/32, 83-72987/32, 29348D/17 and 06733V/05 refer to 8-carboxyamino tetralins. Additional 07833V/05 refers to 8-amido and 8-alkylamido tetralin.

EPO patent application EPO 270 947 (1988) discloses 8-hydroxy and 8-methoxyletralins.

EPO patent application EPO 0 272 534 (1988) discloses aminotetralins including 8-amido compounds.

The references cited herein are disclosures describing work related to the invention:

Hjorth, S.; Carlsson, A.; Lindberg, P.; Sanchez, D.; Wikstron, H.; Arvidsson, L.-E.; Hacksell, U.; Nilsson, J. L. G., *J. Neural Transm.*, 1982, 55, page 169.

Mellin, C.; Bjork, L.; Karlen, A.; Johansson, A. M.; Sundell, S.; Kenne, L.; Nelson, D. L.; Alden, N.-E.; Hacksell, U., *J. Med, Chem.*, 1988, 31, page 1130.

Cossery, J. M.; Gozlan, H.; Spampinato, U.; Perdicakis, C.; Guillaumet, G.: Piehat, L.; Hamon, M., *European J. Pharmacol.*, 1987, pages 140, 143.

Trans-7- and trans-9-hydroxy-1,2,3,4,4a,5,6,10b-octahydrobenzo [f]quinolines have been synthesized and their effects on central dopamine and α-receptors have been studied. Arvidsson, L.-E. et at, *J. Med. Chem*, 1983, 27, page 45.

Octahydrobenzo-isoquinolines are also described in Derwent 84-073373/13.

Hexahydrobenzo-isoquinolines are described in Derwent 55370A/31 (DT 2801 576).

Derwent 83-840180/50 and 86-298374/45 discloses tetrahydro-benzo-isindoline derivatives which interact specifically with various androgenic receptors and are useful for treating hypertension. 86-298374/45 also discloses that the compounds also have sedative activity.

French patent 1.555.553 (Derwent 37216 describes 2,3,4,4a,5,6-hexahydrobenzo[f]quinolines.

U.S. Pat. No. 4,622,405 discloses 1,2,3,3α,8,8α-hexahydro indero(1,2-C)pyrroles(s).

Derwent 63503T-B, 52201R-B, 23543R, 30016 and 41102 disclose hexahydroinenopyridinols.

Derwent 67323W/41 discloses benzoisoindolines as anti-aggressive and analgesic agents.

SUMMARY OF THE INVENTION

This invention encompasses compounds of Formula I

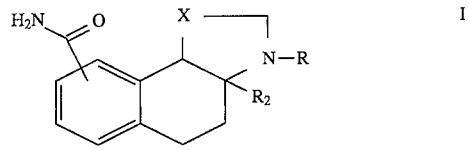

wherein X is $-(CH_2)_n-$ or $-C(R_1)(H)-$; R is $C_1-C_8$ alkyl; $R_1$ and $R_2$ are the same or different and are selected from the group consisting of hydrogen, $C_1-C_8$ alkyl, $C_2-C_8$ alkenyl, $C_2-C_8$ alkynyl, aryl and benzyl; and n is 1 or 2; and pharmaceutically acid addition salts thereof.

Preferred compounds are those of Formula Ia.

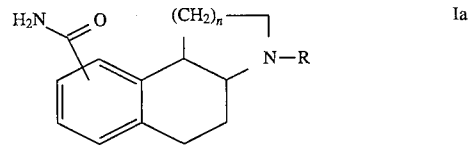

wherein R and n are the same as above.

Most preferred are the compounds of Formula Ib.

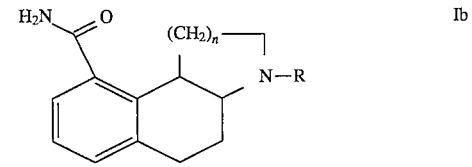

wherein R and n are the same as above.

The 9-carboxamido, (Formula Ib) compounds of this invention wherein n is 1, and the 10 carboxamido (Formula Ib) compounds wherein n is 2, possess selective pharmacological properties and are useful in treating central nervous system disorders including depression, anxiety, panic attacks, obsessive-compulsive disturbances, senile dementia, emotional disturbances related to dementia disorders, stroke, trauma, migraine and stimulation of sexual activity. These compounds are also useful to alleviate aggressive behavior, confusional delirious states and impotence.

The 6, 7 and 8 carboxamide compounds of the invention wherein n is 1 and the 7, 8, 9 carboxamido compounds wherein n is 2 possess selective pharmacological properties and are useful in treating schizophrenia and Parkinson's disease.

In addition to their central nervous system pharmacological activities, the compounds of this invention are also useful in treating hypertension, congestive heart failure and cardiac arrythmias. Processes for preparation of these compounds, their pharmaceutical use and pharmaceutical preparations employing such compounds constitute further aspects of the invention.

An object of the invention is to provide compounds for therapeutic use, especially compounds having a therapeutic activity in the central nervous system via an interaction at 5-HT$_{1A}$ receptors in mammals including man. The compounds of this invention have been found to have unexpectedly superior resistance to liver metabolism and have excellent oral plasma bioavailability.

This invention also encompasses compounds of Formula II

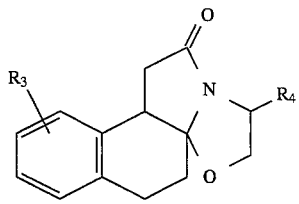

wherein $R_3$ is hydrogen, halogen, $C_1$–$C_8$ alkyl and $C_1$–$C_8$ alkoxy; and $R_4$ is phenyl, $C_1$–$C_8$ alkyl and benzyl; which is an important intermediate for preparing compounds of formula I.

DETAILED DESCRIPTION OF THE INVENTION

The compounds of this invention are identified in two ways: by the descriptive name and reference to labelled structures contained in appropriate charts. In appropriate situations, the proper stereochemistry is also represented in the charts.

In this document file parenthetical term ($C_n$–$C_m$) is inclusive such that a compound of ($C_1$–$C_8$) would include compounds of one to 8 carbons and their isometric forms. The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl and n-octyl.

Alkoxy as represented by —OR$_1$ when R$_1$ is ($C_1$–$C_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, isohexoxy, n-heptoxy, isoheptoxy, and n-octoxy.

Alkenyl refers to a radical of m aliphatic unsaturated hydrocarbon having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2hexenyl, 3-hexenyl, 4-hexenyl, 1-methyl-4-hexenyl, 3-methyl-1-hexenyl, 3-methyl-2-hexenyl, 1heptenyl, 2-heptenyl, 3-heptenyl, 4-heptenyl, 1-methyl-4-heptenyl, 3-methyl-1-heptenyl, 3-methyl-1-heptenyl, 3-methyl-2-heptenyl, 1-octenyl, 2-octenyl, or 3-octenyl.

Alkynyl refers to a radical of an aliphatic unsaturated hydrocarbon having a triple bond and includes ethynyl, propynyl, butynyl, pentynyl, hexynyl, heptynyl and octynyl.

Aryl means

Halogen is bromine, chlorine, flourine and iodine.

LDA is lithium diisopropyl amide.

It will be apparent to those skilled in the an that compounds of this invention may contain chiral centers. The scope of this invention includes all enantiomeric or diastereomeric forms of Formula I compounds either in pure form or as mixtures of enantiomers or diastereomers. The compounds of Formula I contain two asymmetric carbon atoms in the aliphatic ring moiety, including the ring carbon atoms adjacent to the nitrogen atom. The therapeutic properties of the compounds may to a greater or lesser degree depend on the stereochemistry of a particular compound. Pure enantiomers as well as enantiomeric or diastereomeric mixtures are within the scope of the invention.

The compounds of this invention may be obtained by one of the following methods described below and outlined in the appropriate charts.

The carboxamido-(1,2N)-carbocyclic 2-aminotetralins of this invention can be made in accordance with the processes illustrated in Charts A, B, C, D and E.

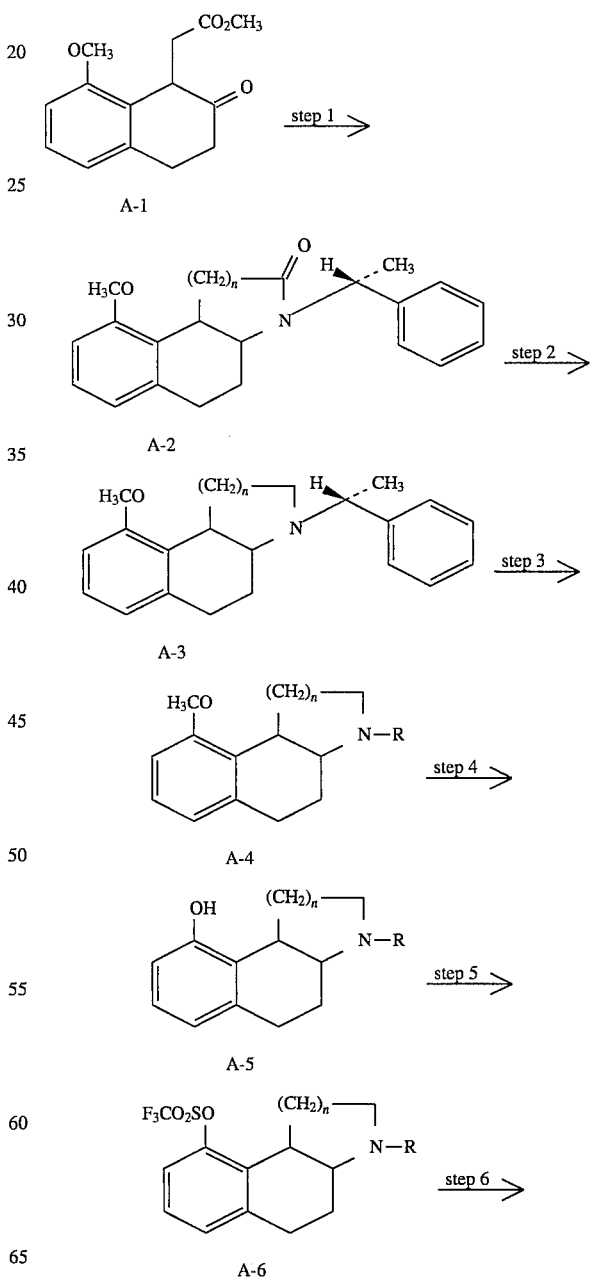

-continued
Chart A:

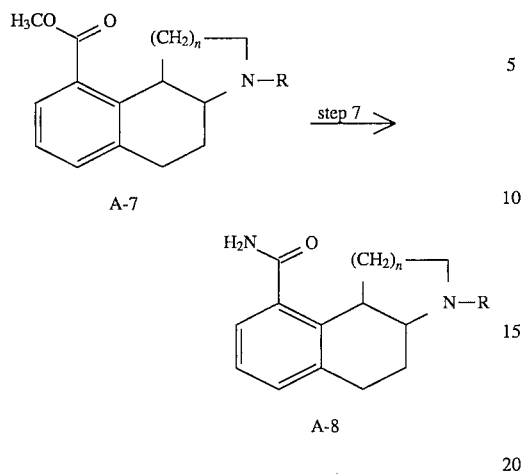

In step 1, A-1 (1,2,3,4-tetrahydro-8-methoxy-2-oxo-1-naphthalene acetic acid methyl ester, is reductively aminated with R-(+)-methylbenzyl amine in methanol/tetrahydrofuran in the presence of sodium cyanoborohydride at pH<5. A process for the preparation of 1,2,3,4,-tetrahydro-8-methoxy-2-oxo-1-naphthalene acetic acid methyl ester is described in preparation 3 and Chart B of application PCT/US90/03551 filed Jun. 27, 1990 and published Jan. 24, 1991. In step 2, A-2 is reduced with an lithium aluminum hydride in tetrahydrofuran to yield diastereomers A-3. The diastereomers A-3 were separated by liquid chromatography. In step 3, each diastereomer is independently debenzylated using 1-chloroethylchloroformate in chlorobenzene. The secondary amine is acylated with the appropriate acyl chloride in triethylamine and methylene chloride then reduced with lithium aluminum hydride/aluminum chloride complex in tetrahydrofuran to yield A-4 as optically pure material. In step 4, A-4 demethylated with diphenylphosphine and n-butyl lithium in tetrahydrofuran to yield the 8-hydroxy compound A-5. In step 5. the 8-OH derivative A-5 is reacted with triflic anhydride in the presence of pyridine in methylene chloride to provide A-6. In step 6, A-6 is reacted with palladium acetate and bis(diphenylphosphino)propane in methanol/dimethyl formamide in the presence of gaseous carbon monoxide to yield the 8-carboxy methyl ester A-7. In step 7, A-7 is first hydrolyzed to the carboxylic acid with sodium hydroxide reflux, which is coupled with gaseous ammonia in the presence of diethylcyanophosphonate, triethylamine in dimethylformamide to give the 8-carboxamide derivative A-8.

Chart B:

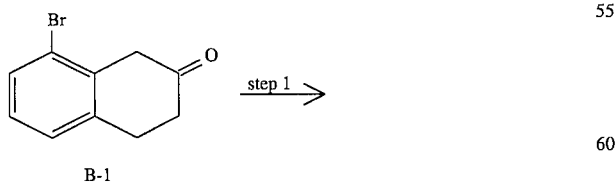

-continued
Chart B:

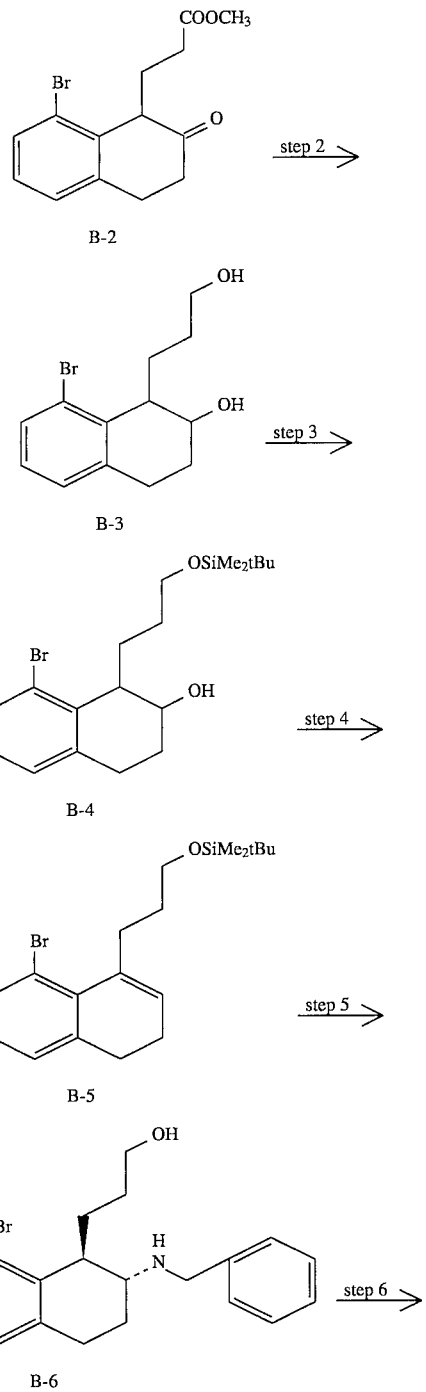

-continued
Chart B:

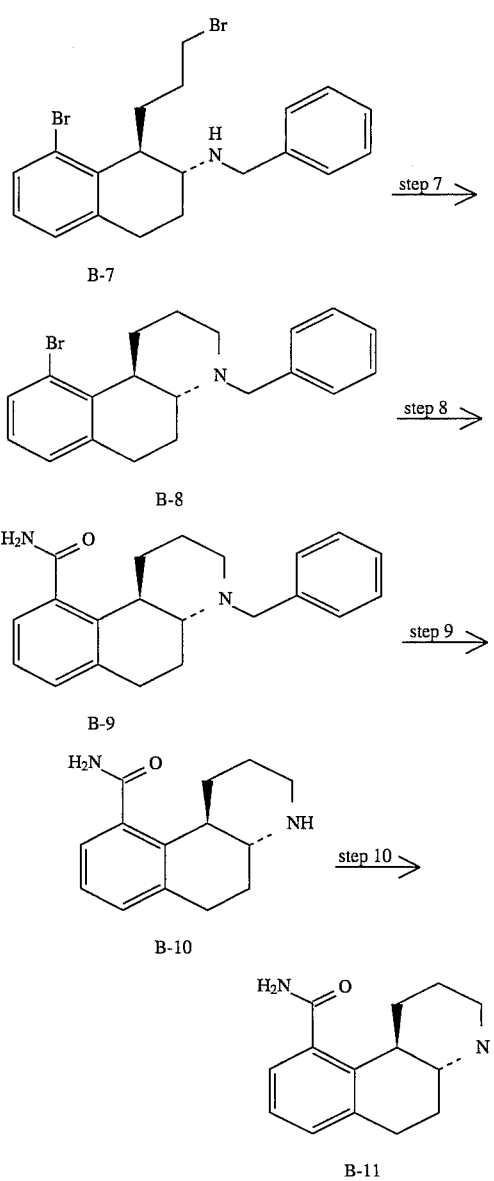

enantiomer of B-8. In step 8, B-8 (the racemate, (+)-, or (−)-enantiomer) is reacted with t-butyllithium and trimethylsilylisocyanate in tetrahydrofuran to yield B-9. In step 9. B-9 (the racemate, (+)-, or (−)-enantiomer) is debenzylated in ethanol in the presence of palladium hydroxide on carbon and hydrogen to yield B-10. In step 10, B-10 (the racemate, (+)-, or (−)-enantiomer) is alkylated with the appropriate alkyl halide in acetonitrile in the presence of potassium carbonate to yield B-11.

The 5, 6 and 7 carboxmides (7, 8 and 9 wherein n=2) of the invention can be prepared by substituting the appropriately substituted methoxy compound for the 8-epoxy (9-epoxy when n=2) compound (A-1) in step 1 of the process of Chart A. These methoxy compounds are readily available or can be made by methods known in the art.

Chart C:

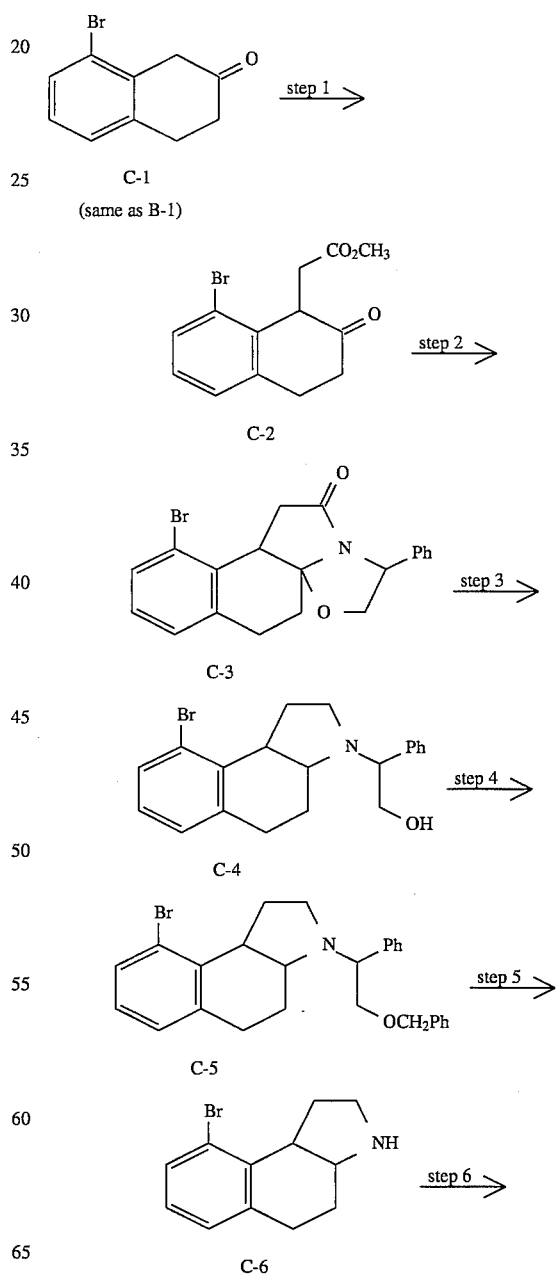

In step 1, B-1 (8-bromo-1,2,3,4-tetrahydro-2-oxonaphthalene, a compound known in the art) is alkylated with 3-bromopropionate in tetrahyrofuran in the presence of lithium diisopropylamide to yield B-2. In step 2, B-2 is reduced with lithium aluminum hydride in diethylether to yield B-3. In step 3. B-3 is mono-silylated in dimethylformamide with t-butyldimethylsilyl chloride in the presence of imidazole to yield B-4. In step 4, B-4 is mesylated in methylene chloride with methanesulfonyl chloride in the presence of triethylamine and then the resulting mesylate is eliminated in acetonitrile in the presence of 1,8-diazabicylo [5.4.0]undec-7-ene to yield B-5. In step 5, B-5 is aminated in benzene with benzyl azide in the presence of dichloroborane methyl sulfide complex and boron trichloride to yield B-6. In step 6, B-6 is refluxed with 48% hydrobromic acid to yield B-7. In step 7, is cyclized in acetonitrile in the presence of potassium carbonate to yield racemic B-8. B-8 is resolved with (+)-di-p-toluoyl-D-tartaric acid in methanol to yield the pure (−)-enantiomer of B-8, and with (−)-di-p-toluoyl-L-tartaric acid monohydrate to give the pure (+)-

11
-continued
Chart C:

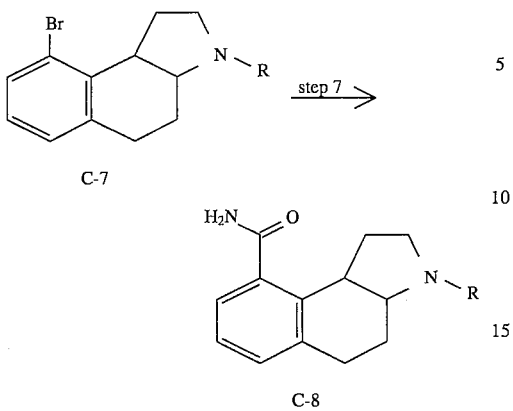

C-7

C-8

The process of Chart C is the preferred method of preparing compounds of Formula I. In step 1, C-1 (8-bromo-1,2,3,4-tetrahydro-2-oxonaphthalene) is alkylated with methyl bromoacetate using lithium diisopropyl amide in tetrahydrofuran to give C-2. In step 2, C-2 is condensed with phenylglycinol in refluxing toluene with azeotropic removal of water to give the tetracycle C-3. In step 3, C-3 is reduced with borane in tetrahydrofuran to provide the aminoalcohol C-4. In step 5, the hydroxyl of C-4 is alkylated with benzyl chloride using potassium hydroxide in dimethyl sulfoxide to give the ether C-5. In step 5, the benzylic C-N bond of C-5 is cleaved by treatment with 1-chloroethyl chloroformate in chlorobenzene and subsequent methanolysis to give the secondary amine C-6. In step 6, the amine of C-6 is alkylated using propionic acid and sodium borohydride to give C-7 (R=propyl). In step 7, C-7 is reacted with t-butyllithium and trimethylsilylisocyanate in tetrahydrofuran to give C-8 (R=propyl).

Chart D:

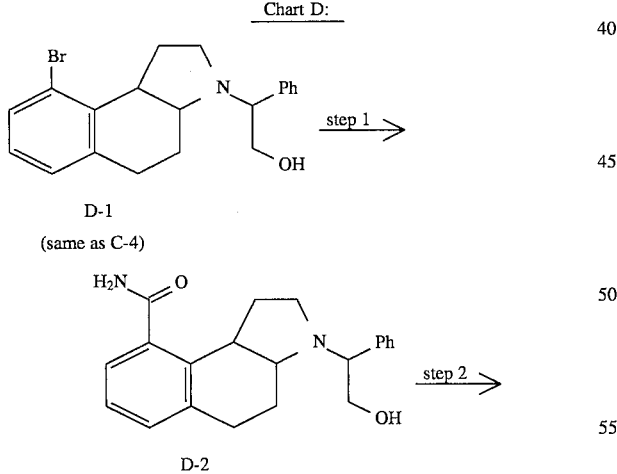

D-1
(same as C-4)

D-2

12
-continued
Chart D:

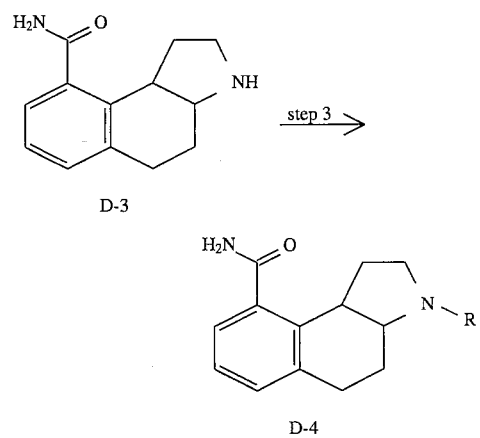

D-3

D-4

In step 1, cis-(±)-2,3,3a,4,5,9b-hexahydro-9-bromo-3-(2-R-hydroxymethylbenzyl)-1-H-benz[e]indole (D-1) is treated with palladium acetate and 1,3-bis-diphenylphosphinopropane in a mixture of dimethylformamide, diisopropylethylamine, and hexamethyldisilylazane at 100° C. under an atmosphere of carbon monoxide to give the aryl amide D-2. In step 2, D-2 was hydrogenolyzed using 20% palladium on carbon in absolute ethanol under 45 psi of hydrogen at 50° C. to give the secondary mine D-3. In step 3, D-3 was alkylated with bromopropane in dimethylformamide/acetonide in the presence of potassium carbonate to give D-4 (R=propyl).

Chart E:

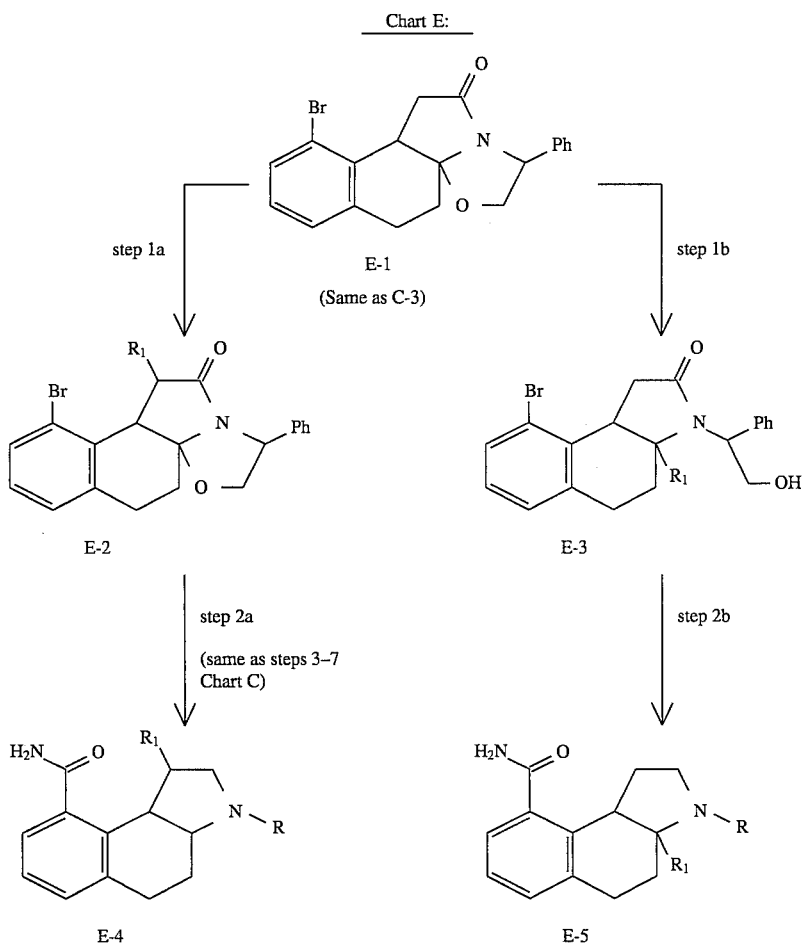

Chart E illustrates some of the utility of the valuable synthetic intermediate C-3. In step 1a, [4bS-(4b.alpha., 8.beta., 10aR*)]-4-bromo-4b.5,8,9,11,12-hexahydo-8-phenyl-6H-benz[e]oxazolo[2,3-i]indol-6-one (E-1, same as C-3) is alkylated using lithium hexamethyldisilazane in tetrahydrofuran to give E-2. In step 2a, E-2 is converted to the final product E-4 by carrying out steps 3 through 7 of Chart C. In step 1b, E-1 is treated with titanium tetrachloride and an appropriate nucleophile (e.g., allyltrimethylsilane) in dichloromethane at −78° C. to room temperature to give the lactam E-3 (example where R1 is allyl). In step 2b, E-3 is carried through the sequence of reactions described in Example 4 below to provide E-5.

In clinical practice the compounds of the present invention will normally be administered orally, rectally, or by injection, in the form of pharmaceutical preparations comprising the active ingredient either as a free base or as a pharmaceutically acceptable non-toxic, acid addition salt in association with a pharmaceutically acceptable carrier. Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. These salts are readily prepared by methods known in the art. The use and administration to a patient to be treated in the clinic would be readily apparent to a person of ordinary skill in the art.

In therapeutical treatment the suitable daily doses of the compounds of the invention are 0.1–2000 mg/kg for oral application, preferably 0.5–500 mg/kg, and 0.1–100 mg/kg for parenteral application, preferably 0.5–50 mg/kg.

The compounds of Formula Ia of this invention are very selective 5-$HT_{1A}$ receptor agonists having generally little or no dopaminergic activity. These compounds are particularly effective anxiolytic and antidepressant agents. Other uses for these compounds include panic attacks, obsessive-compulsive disturbances, and senile dementia particularly the emotional disturbances seen in dementia disorders. In addition, central 5-HT receptor activation are believed to be involved in mediating sexual behavior. These compounds would be useful to stimulate sexual activity and to alleviate impotence. The compounds of this invention are also useful to alleviate aggressive behavior, confusional delirious states.

It has been found that the compounds of the present invention and pharmacologically acceptable salts thereof have unexpectedly superior resistance to liver metabolism and excellent oral plasma bioavailability. Generally aminotetralins possessing 5-$HT_{1A}$ agonist activity are rapidly metabolized by the liver and have poor oral plasma bioavailability. The excellent oral bioavailability of compounds contained in this invention results in good potency and long duration of action following oral administration of the compounds. Both these features are beneficial to effective clinical treatment.

The utility of the compounds of this invention to treat central nervous system disorders is shown in behavioral, physiological and biochemical tests. The methods are given as follows:

Binding: Inhibition of 8-OH-DPAT binding in a bovine brain homogenate. Potency is given as nM dose required to inhibit 50% of DPAT binding (IC50). This test measures ability to bind to 5-hydroxytryptamine (5-HT$_{1A}$) receptor.

Hypothermia: Starting with a dose of 30 mg/kg, four mice are injected subcutaneously with test compound. Twenty minutes later, the number of animals whose body temperature has decreased by 2° C. or more are counted. If all four animals reach criteria, the drug is considered "active", and subsequent readings are taken at 60 and 120 minutes after drug. The time for last statistically significant drug affect on mean body temperature is indicated in minutes. For all "active" compounds, doses are lowered by 0.5 log intervals until a dose which does not lower body temperature by 2° C. in any animal is found. Active compounds are retested using oral administration. Potency is given as mg/kg ED50 (dose required to depress temperature in two of four mice) as measured by Spearman-Karber statistics.

Sympathetic Nerve Discharge (SND): The i.v. mg/kg dose causing a 50% depression in SND in chloralose anesthelized cats and the maximum inhibition of sympathetic activity observed in the dose range tested (0.001–1.0 mg/kg i.v.).

BP SND/MAX: The blood pressure of the chloralose anesthetized cats in percent control at the dose causing 50% depression in SND and the maximum reduction in blood pressure as percent of the control blood pressure in the same animals observed in the dose range tested (0.001–1.0 mg/kg i.v.).

5-HT Cell Firing: The i.v. mg/kg dose causing a 50% depression in the firing of dorsal raphe 5-HT cell firing in chloral hydrate anesthetized rats.

Invitro Rat Hepatocyte: Intrinsic clearance of 3 concentrations of compound (2, 5 and 15 μg/ml)following a 60 minute incubation at 37° C. in the presence of a suspension of freshly prepared rat hepatocytes (5.0 million cells/ml). Aliquots of each incubate were withdrawn at preset times during the incubation and analyzed for parent compound using HPLC methodology. Intrinsic clearance is expressed as ml/min/5 million cells and metabolic stability relative to cis-(±)-2,3,3a,4,5,9b-hexahydro-9-carboxamide-3-(n-propyl)-1H-benz[e]indole is determined.

Pharmacokinetics Following Constant Infusion: Clearance rate (ml/min/kg) was determined following a 12 hour infusion (300 μg/hour) of compound in the anesthetized rat. Disappearance of parent compound from plasma was measured at multiple time points following cessation of the infusion using HPLC methodology.

Oral Bioavailability: Comparison of the disappearance of compound from plasma following oral (6 mg/kg) and intravenous (2 mg/kg) administration in conscious rats. Parent compound in plasma was measured at multiple time points following administration using HPLC methodology. Bioavailability is expressed as a percentage of the drug in plasma following oral administration compared to that following intravenous administration. Results are as follows:

| Compound | Name |
|---|---|
| 1 | cis-(+)2,3,3a,4,5,9b-hexahydro-9-carboxamido-3-(n-propyl)-1H-benz[e]indole |
| 2 | cis-(−)2,3,3a,4,5,9b-hexahydro-9-carboxamido-3-(n-propyl)-1H-benz[e]indole |
| 3 | cis-(+)2,3,3a,4,5,9b-hexahydro-9-carboxamido-3- |

| Compound | Name |
|---|---|
| | (n-propyl)-1H-benz[e]indole |
| 4 | trans-(+)1,2,3,4,4a,5,6,10b-octahydro-10-carboxamido-4-(n-propyl)-benzo[f]quinoline |
| 5 | trans-(−)1,2,3,4,4a,5,6,10b-octahydro-10-carboxamido-4-(n-propyl)-benzo[f]quinoline |
| 6 | trans-(+)1,2,3,4,4a,5,6,10b-octahydro-10-carboxamido-4-(n-propyl)-benzo[f]quinoline |

Binding at the 5-HT$_{1A}$ receptor site. Data expressed as the IC50 (nM).
Compound 1:5.2
Compound 2:10.2
Compound 3:533
Compound 4:3.7
Compound 5:1.5

Mouse hypothermia. Data expressed as ED50 values (mg/kg) following subcutaneous and oral administration.
Compound 1:0.97 (s.c.), 7.3 (p.o.)
Compound 4:0.23 (s.c.), 4.1 (p.o.)
Compound 5:1.73 (s.c.)

Sympathetic nerve discharge. Data expressed as ED50 dose (mg/kg, i.v.) which inhibits spontaneous sympathetic activity.
Compound 1:0.037
Compound 2:0.019
Compound 3:>1.0
Compound 5:0.15

Percent of control arterial blood pressure following the dose of compound which inhibited sympathetic activity by 50%.
Compound 1: 82%
Compound 2: 84%
Compound 5:85 %

Depression of 5-HT cell firing expressed as ED50 (mg/kg, i.v.)
Compound 1:0.002
Compound 2:0.006
Compound 3:>0.3
Compound 5:>0.1

In vitro hepatocyte assay: data expressed as clearance (ml/min/5 million cells) and as relative metabolic stability to cis-(±)2,3,3a,4,5,9b-hexahydro-9-carboxamido-3-(n-propyl)-1H-benz[e]indole.
Compound 1:0.013 (clearance), rel. stab.: 1.0
Compound 6: rel. stab.: 1.05
Compound 5:0.012 (clearance), rel. stab.: 3.59

In vivo steady state clearance: data expressed as ml/min/kg.
Compound 1:58
Compound 5:43

Oral plasma bioavailability expressed as % following oral and i.v. dose. Compound 1: Study 1:59%; Study 2:70%. In the second study samples were taken for 24 hours following administration of compound and therefore is a more accurate determination of bioavailability. Compound 5: 86%
In comparison the plasma oral bioavailability of 8-OH DPAT is <5%

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate varia-

Preparation 1:
Cis-(+−)-1,3,3a,4,,9b-hexahydro-9-methoxy-3-(2-R-methylbenzyl)-2H-benz[e]indol-2-one (A-2, Chart A)

A solution of 15.9 g (64 mmol) 1,2,3,4-tetrahydro-8-methoxy-2-oxo-1-naphthalene acetic acid methyl ester (A-1) and 41.3 mL (320 mmol) R-methylbenzyl amine in methanol/tetrahydrofuran was cooled to 0° C. and 40 ml acetic acid was added After 10 min, 8.05 g (128 mmol) sodium cyanoborohydride was added. The solution was stirred for two day and an additional 4 g of sodium cyanoborohydride was added. After stirring overnight, the reaction was quenched with 1N sodium hydroxide and solvents removed in vacuo. The solution was extracted with (3×500 mL) ethyl acetate. The combined organic layers were washed with brine, dried (MgSO$_4$), filtered and evaporated to yield a brown oil. The oil was flash chromatographed on 1 kg silica gel 60 (230–400 mesh) eluting with hexane/ethyl acetate (3:1) to remove the non-polar impurities and hexane/ethyl acetate (1:1) to give the desired product. Homogeneous fractions were combined and concentrated to yield an oil as the title compound A-2 (11.17 g, 54.4%) 1HNM (CDCl$_3$, TMS)δ7.43–7.27 (m,5H); 7.11–7.06 (t, J=9 Hz, 1H), 6.68–6.62 (m, 2H), 5.57–5.50 (q, J=6 Hz, 1H), 3.78 (s, 3H), 3.42–2.08 (m, 5H), 1.68–1.61 (dd, J=6 Hz, 6H), 1.23 (t, J=7 Hz, 3H).

Preparation 2:
cis-(+−)-2,3,3a,4,5,9b-hexahydro-9-methoxy-3-(2-R-methylbenzyl)-1H-benz[e]indole (A-3, Chart A)

To a suspension of lithium aluminum hydride in 300 mL THF at 0° C. was added 11.17 g (34.79 mmol) of A-2 in 200 mL tetrahydrofuran. The solution was brought to reflux (bath temp 85°–90° C.) overnight. The solution was quenched in a 2L Erlenmeyer flask at 0° C. with saturated sodium sulfate then diluted to 2L using tetrahydrofuran. The solution was dried using sodium sulfate and magnesium sulfate, filtered and concentrated to yield a brown oil. The oil was chromatographed on 1 kg silica gel 60 (230–400 mesh) eluting with hexane/ethyl acetate (4:1). The diastereomers were separated and collected in three portions (A-pure, mixture A+B, and B–pure). the mixed fractions were purified again on 1 kg silica gel 60 (230–400 mesh) eluting with hexane/ethyl acetate (12:1). The homogeneous fractions were combined to obtain Pure A (less polar) and Pure B (more polar) products. (The reactions described in Preparation 1 and 2 were repeated and the products from these reactions combined to yield 4.1 g of pure A-3A and 8.78 g of pure A-3B as title compounds.)

A-3A:1HNMR (CDCl$_3$,TMS)δ7.37–7.19 (m, 5H), 7.07–7.01 (t, J=9 Hz, 1H), 6.69–6.64 (t, J=7 Hz, 2H), 3.85–3.74 (q, J=7 Hz, 1H), 3.77 (s, 3H), 3.39–3.30 (q, J=9 Hz, 1H), 2.99–2.94 (m, 1H), 2.81–2.63 (m, 3H), 2.53–2.41 (m, 2H), 1.76–1.70 (m, 2H), 1.43–1.41 (d, J=7 Hz, 3H). [α]$_D$=+46° (c 1.21, meOH) taken as the HCL salt)

A-3B:1HNMR (CDC13, TMS)δ7.41–7.22 (m, 5H), 7.07–7.02 (t, J=9 Hz, 1H), 6.68–6.65 (m, 2H), 3.79 (s, 3H), 3.43–3.379 (q, J=9 Hz, 1H), 3.22–3.15 (q, J=7 Hz, 1H), 2.81–2.42 (m, 5H), 1.60–1.46 (m, 3H), 1.43–1.41 (d, J=7 Hz, 3H). [α]$_D$=+9.31° (c 1.02, MeOH) (taken as the HCl salt).

Preparation 3:
cis(−)-2,3,3a,4,5,9b-hexahydro-9-methoxy-3-(n-propyl)-1H-benz[e]-indole (A-4, Chart A)

A solution of 4.98 g (16.2 mmol) A-3B, 16 mL 1-cloro-ethylchloroformate in 100 mL chlorobenzene was refluxed under nitrogen. After 2 days, the mixture was concentrated in vacuo to half of it's original volume. It was treated with 80 mL methanol and refluxed (bath temp 140° C.) for 1 h. The solvent was removed in vacuo to give a brown oil. The oil was dissolved in 80 mL methylene cloride and treated with 13.5 mL, (97.2 mmol) triethylamine followed by 2.8 mL (32.4 mmol) propionyl chloride at room temperature. After stirring for 2 h, about 2 mL methanol was added and stirred for 1 h. The reaction was quenched with 10% sodium hydroxide and extracted with methylene chloride (2×600 mL). the combined organic layers were waslied with water, brine, dried (MgSO$_4$), filtered, and concentrated in vacuo to yield a brown oil. The oil was purified by liquid chroniatography on 400 g silica gel 60 (230–400 mesh), eluting with hexane/acetone (2:1) and collecting 40 mL fractions. Homogeneous fractions were collected to yield 3.4 g of a light brown oil as the pure n-propionate. A suspension of lithium aluminum hydride (0.95 g, 25 mmol) in 200 mL tetrahydrofuran was cooled to −20° C. under a nitrogen atmosphere was treated with 5.3 g (39.6 mmol) aluminum chloride powder via a powder froreel over 5 min. The mixture was stirred for 10 minutes and the brown oil obtained above was added slowly over 30 minutes in 60 mL tetrahydrofuran. The mixture was allowed to warm to 0° C. over 1 h and quenched with 10% sodium hydroxide, 500 mL water added and extracted with 2 X1L methylene chloride. The organic layer was washed with brine, dried (MgSO$_4$) filtered and concentraed to give an oil. The crude product was purified by liquid chromatography on 400 g silica gel 60 (230–400 mesh) eluting with hexane/acetone (2:1) and collecting 40 mL fractions. Homogeneous fractions were collected to yield a light yellow oil (A-4B, 2.42 g, 78.8%). For analysis, a small portion was converted into the HCl salt and recrystallized from ethyl acetate/methanol/hexane to give the title compound as a white solid: mp 150°–151° C.; [α]$_D$=−37.3° (c 0.55, CHCl$_3$). 1HNMR (CDCl$_3$, TMS)δ7.15–6.71 (m, 3H); 4.0(m,1H); 3.83 (s,3H); 3.65–1.75 (m, 13H), 1.03 (t,J=7 Hz, 3H).

A-4A was also prepared in a manner identical to the above but using A-3A to yield (+) enantiomer: mp 150–151 C.; [α]$_D$=+36.5° (c 0.57, CHCl$_3$) The 1HNMR was identical with that of A-4B.

Preparation 4:
cis-(−)-2,3,3a,4,5,9b-hexahydro-9-hydroxy-3-(n-propyl)-1H-benz[e]-indole (A-5B, Chart A)

A solution of 4.9 mL (28.2 mmol) diphenylphosphine in 10 mL tetrahydrofuran was treated with 17.6 mL (28.2 mmol) n-butyl lithium at 0° C. over a 30 min period under a nitrogen atmosphere. The red solution was stirred at room temp for 10 min and 2.3 g(9.4 mmol) A-4B in 10 mL THF was added. The reaction was refluxed (bath temp 80° C.) for 18 h, and then quenched with 400 mL water and extracted with 2 L ethyl acetate. The organic layer was washed with water, brine, dried (MgSO$_4$), filtered and concentrated. The crude oil was purified by liquid chromatography on 400 g silica gel 60 (230–400 mesh) eluting with 2 L methylene chloride followed by methylene chloride/acetone (1:1) and collecting 40 mL fractions. Homogeneous fractions were combined and concentrated to yield a light yellow oil A-5B (2.13 g, 98%) For analysis, the HCl salt was formed on a small portion and recrystalized from methanol/ethyl acetate to yield the title compound as a white solid: mp 183°–184° C.; $[\alpha]_D=-58.7°$ (c 0.61, CHCl$_3$); 1HNMR (CD30D, TMS)δ 7.08–6.60 (m, 3H); 4.06–1.72 (m, 14H): 1.06 (t, J=7 Hz,3H).

A-5A was also prepared in an identical manner using A-4A to yield the (+) enantiomer: mp 183°–184° C.$[\alpha]_D=$ +58° (c 0.52, CHCl$_3$). 1HNMR (CD30D, TMS) δ7.08–6.60 (m, 3H); 4.06–1.72 (m, 14H); 1.06(t,J=7 Hz, 3H).

Preparation 5: cis-(+—)-2,3,3a,4,5,9b-hexahydro-9-(trifluoromethanesulfonyloxy)-3-(n-propyl)-1H-benz[e]indole (A-6, Chart A)

A solution of 3.11 g (13.5 mmol) of the 8-OH compound (A-5, racemic) in 100 mL methylene chloride was stirred with pyridine (6.55 mL, 81 mmol) at 0° C. under a nitrogen atmosphere. Triflic anhydride (6.81 mL, 40.5 mmol) was added by dropping funnel as a solution n 30 mL methylene chloride over a 30 min period. The mixture then warmed to rt and stirred for an additional hour. The reaction mixture was quenced with NaHCO3 (satd) to pH>5, then extracted with methylene chloride (4×300 mL). The combined organic layers were washed with brine, dried (MgSO$_4$), filtered and concentrated to yield an oil. The oil was flash chromatographed using 500 silica gel 60 (230–400 mesh) and eluting with hexane/ethyl acetate 2:1. Homogeneous fractions were combined and concentrated to yield the title compound A-6 as an oil (3.32 g, 68%) 1HNMR (CDCl$_3$, TMS)δ7.17–7.07 (m,3H), 3.59–3.50 (q, J=9 Hz, 1H); 3.13–3.07 (t, J=7 Hz, 1H); 2.93–1.47 (m, 12H); 0.95–0.91 (t, J=Hz, 3H).

The (–)-enantiomer was prepared in a similar procedure as above using A-5B as the starting material to yield the title compound A-6B as a light yellow oil. The 1HNMR (CDCl$_3$, TMS) was identical to above.

The (+)-enantiomer was prepared in a similar procedure as above using A-5A as the starting material to yield the title compound A-6A as a yellow oil. The 1HNMR (CDCl$_3$, TMS) was identical to above.

Preparation 6: cis-(+—)-2,3,3a,4,5,9b-hexahydro-9-carbomethoxy-3-(n-propyl)-1H-benz[e]indole (A-7,Chart A)

A solution of 3.27 g (9 mmol) triflate A-6 and 2.5 mL (18 mmol) triethylamine in 10 mL methanol and 30 mL DMF was degassed with nitrogen through a syringe (10 min). Carbon monoxide was then introduced mid bubbled for 10 min. During this time, a solution of 202 mg (0.9 mmol) palladium acetate and 445 mg (1.08 mmol) 1,3-bis(diphenylphosphino)propane in 10 mL DMF was dissolved and degasseal with for 10 min with nitrogen. This solution was added to the reaction, heated to 70° C. and carbon monoxide bubbled through the refluxing solution overnight. Nitrogen was bubbled through the solution and then it was quenched with NaHCO3 (satd). The mixture was extracted with ethyl acetate (3×500 mL) and the combined organic layers were washed with brine, dried (MgSO4), filtered and concentrated to yield an oil. The oil was flash chromatographed on 500 g silica gel 60 (230–400 mesh) eluting with hexane/ethyl acetate (4:1). Homogeneous fractions were combined and concentrated to yield the title compound A-7 as an oil (1.9 g, 77.5%): NMR (CDCl$_3$, TMS)δ7.65–7.62(d,J=9 Hz, 1H); 7.26–7.08 (m, 2H) 4.18–4.09 (q,J=9 Hz, 1H); 3.87 (s, 3H); 3.08-1.37 (m, 13H); 0.95–0.90 (t, J=7 Hz, 3H).

The (–)-enantiomer was prepared in a similar procedure as above using A-6B as the starting material to yield the title compound A-7B as an light yellow oil. The 1HNMR (CDCl$_3$, TMS) was identical to above (A-7).

The (+)-enantiomer was prepared in a similar procedure as above using A-6A as the starting material to yield the title compound A-7A as a yellow oil. The 1HNMR (CDCl$_3$, TMS) was identical to above (A-7)

Preparation 7:
8-bromo-1,2,3,4-tetrahydro-2-oxo-naphthalenepropionic acid methyl ester (B-2, Chart B)

A solution of 8-bromo-1,2,3,4-tetrahydro-2-oxonaphthalene (B-1, 45.02 g, 0.20 mol) in tetrahydrofuran (400 mls) was cooled to –78° C., and a solution of lithium diisopropylamide in cyclohexane (1.5 M, 150 mls, 0.225 mol) was added over a 7 minute period. The mixture was stirred at –78° C. for 10 minutes, the cold bath was removed, and the mixture was stirred for an additional 30 minutes. 3-Bromopropionate (40.1 g, 0.24 mol) was added via a syringe over a 1 minute period. The mixture was stirred at 0° C. for 19 hours, diluted with diethylether, and washed with 10% HCl, saturated aqueous NaHCO3, and brine. The solvent was removed under vacuum to leave a dark oil (66.9 g). Purification by flash chromatography (230–400 mesh silica gel; 15–20% ethyl acetate in hexane) gave the title compound as an amber oil (B-2, 39.4 g, 63% yield). NMR (CDCl$_3$, TMS)δ2.12 (t,J=7.7 Hz,2H), 2.35–2.60 (m, 3H), 2.73–2.81 (m,1H), 2.90–3.01 (m,1H), 3.27–3.39 (M, 1H), 3.64 (s,3,OCH$_3$), 3.84 (t,J=7.7 Hz, 1H), 7.08 (t,J=7.7 Hz, 1H), 7.19 (d,J=7.4 Hz, 1H), 7.48 (d,J=7.9 Hz, 1H). IR (Major peaks) 3060, 1738, 1713, 1595, 1563, 1451, 1438, 1219, 1201, 1168, 1128, 798, 778. Mass spec. m+at m/z 310, 312.

Preparation 8:
8-bromo-1,2,3,4-tetrahydro-1-(3-hydroxypropyl)-2-hydroxynaphthalene (B-3, Chart B)

A solution of 8-bromo-1,2,3,4-tetrahydro-2-oxo-naphthalenepropionic acid methyl ester (B-2, 31.12 g, 0.100 mol) in diethylether (100 mls) was added to an ice-cooled suspension of lithium aluminum hydride (8.0 g, 0.21 mol) with stirring. The cold bath was removed, and the mixture was stirred at room temperature for 2 hours. The mixture was cooled in ice, and water (8.0 mls), 15% NaOH (8.0 mls), and water 24.0 mls) were added in succession. The mixture was stirred at room temperature for two hours and filtered. The precipitate was washed with tetrahydrofuran, and the combined flitrate was dried (MgSO$_4$, and the solvent was removed under vacuum to leave the title compound as an oil (B-3, 29.2 g, 100%). NMR (CDCl$_3$, TMS) δ1.35 (m, 1H), 1.7–2.1 (M,5H), 2.7–3.15 (m, 3H), 3.35–3.45 (m, 1H), 3.45–3.57 (m, 1H), 3.57–3.82 (m,2H), 4.0–4.15 (m,1H), 6.9–7.1 (m,2H), 7.38 (dd, 1H). IR (Major peaks) 3345, 3055, 1591, 1559, 1454, 1433, 1060, 767. Mass spec. m+ at m/z 284, 285.

Preparation 9: 8-bromo-1,2,3,4-tetrahydro-1-[3-(t-butyldimethylsilyloxy)propyl]-2-hydroxynaphthalene (B-4, Chart B)

A solution of 8-bromo-1,2,3,4-tetrahydro-1-(3-hydroxypropyl)-2-hydroxynaphthalene (B-3, 29.15 g, 0.10 mol) and imidazole (17.02 g, 0.25 mol) in dimethylformamide (70 mls) was cooled in ice, and t-butyldimethylsilyl chloride (17.3 g, 0.115 mol) was added with stirring. The mixture was allowed to warm to room temperature slowly. After stirring for a total of 18 hours, crushed ice (30 mls) was added, and the mixture was stirred at ambient temperature for 0.5 hour. The mixture was diluted with water (300 mls) and extracted twice with 1:1 diethylether/hexane. The extracts were washed twice with water and once with brine. The solution was dried (MgSO$_4$), and the solvent was removed under vacuum to leave the title compound as an oil (B-4, 42.78 g, 100%). NMR (CDCl$_3$, TMS)δ0.083, 0.099 (twos,6H,Si-CH$_3$), 0.91 (s,9H,Si-tBu), 1.50–1.60(m, 1H), 1.8–2.0(m, 5H), 2.8–3.0(m,2H), 3.19(d,J=4.3 Hz, 1H), 3.48(m,5 lines, 1H), 3.65–3.85 (m,2H), 4.0–4.13 (m,1H), 6.86(t,J=7.6 Hz, 1H), 6.93 (br. d,J=7.6 Hz, 1H), 7.30 (br. d,J=7.5 Hz,1H). IR (Major peaks)3411, 3057, 1592, 1559, 1472, 1463, 1438, 1256, 1100, 1067, 835, 774. CI Mass spec. m+at m/z 399,401.

Preparation 10:
8-bromo-3,4-dihydro-1-[(3-t-butyldimethylsiloyloxy) propyl]naphthalene (B-5, Chart B)

A solution of 8-bromo-1,2,3,4-tetrahydro-1-[3-(t-butyldimethylsilyloxy)-2-hydroxynaphthalene (B-4, 38.62 g, 0.0967 mol) and triethylamine (19.6 g, 0.194 mol) in methylene chloride (220 mls) was cooled in ice, and a solution of methanesulfonyl chloride (14.4 g, 0.126 mol) in methylene chloride (50 mls) was added dropwise. The mixture was stirred at 0° C. for 20 minutes, allowed to stand at −10° C. for 16 hours, and stirred at room teinperature for 3 hours. The mixture was cooled in ice, and water (100 mls) was added. The mixture was stirred at 0° C. for 1 hour, and the layers were separated. The methylene chloride layer was washed with water and dried (MgSO$_4$). The solvent was remover under vacuum to yield the title compound as an amber oil (45.32 g, 98%). NMR (CDCl$_3$, TMS)δ5.0 (m,1H, O-CH). IR (Major peaks) 3058, 3013, 1593, 1561, 1472, 1463, 1439, 1360, 1337, 1176, 1256, 1102, 952, 836, 775. Mass Spec. shows no m+.

The mesylate (45.3 g, 0.0949 mol) was dissolved in acetonitrile (300 mls) and 1,8-diazabicyclo[5.4.0]undec-7-ene(29.3 g, 0.193 mol) was added. The mixture was stirred at reflux under nitrogen in an oil bath maintained at 110°–115° C. for 24 hours. The solvent was removed under vacuum, and the residue was partitioned between diethylether and 5% hydrochloric acid. The ether solution was washed with 5% hydrochloric acid, saturated NaHCO$_3$, and brine. The solution was dried (MgSO$_4$), and the solvent was removed under vacuum to yield the title compound as an amber oil (B-5, 34.7 g, 96%). NMR (CDCl$_3$, TMS)δ0.0 (s,6H,Si-CH$_3$), 0.86 (s,9H,Si-tBu), 1.60 (m,3H), 2.05 (m,2H), 2.60 (br.t,J=7.3 Hz,2H), 2.89 (br. t,J=7.1 Hz, 2H), 3.56 (t,J=6.6 Hz,2H,O-CH$_2$), 6.14 (br. t,J=5.2Hz, 1H,=CH), 6.92(t,J=7.7 Hz, 1H), 7.10 (br. d,J=6.1 Hz, 1H), 7.41 (br. d,J=8.0 Hz, 1H). IR (Major peaks) 3054, 3030, 1623, 1590, 1561, 1552, 1472, 1462, 1439, 1256, 1106, 836, 773. Mass Spec. m+ -tBu at 323, 325.

Preparation 11:
trans-8-bromo-1,2,3,4-tetrahydro-2-(3-hydroxypropyl)-1-[(phenylimethyl)amino]naphthalene (B-6, Chart B)

A solution 8-bromo-3,4-dihydro-1-[(3-t-butyldimethylsilyloxy)propyl]naphthalene (B-5, 19.20 g, 0.0503 mol) in benzene (50 mls) was degassed with argon and cooled in ice. Boron trichloride in hexane (1.0M, 50.3 mls, 0.0503 mol) was added over a 4 minute period. Dichloroborane methylsulfide (7.40 g, 0.0511 mol) was added via a syringe over a 5 minute period. The mixture was stirred at room temperature for 30 minutes and then at rooin teinperature for two hours. The mixture was cooled in ice and benzyl azide (6.7 g, 0.050 mol) was added over a 2 minute period. The mixture was stirred at 0° C. for 15 minutes, room temperature for 1 hour, and was then heated to reflux. The mixture was again cooled in ice, and benzyl azide (6.6 g, 0.050 mol) was added. The mixture was stirred at room temperature for 15 minutes and at reflux for 20 minutes. The mixture was cooled in ice, and water (100 mls) and then 10% hydrochloric acid were slowly added. The mixture was stirred at ambient temperature for 10 minutes and bascified with solid NaOH while cooling in ice. The mixture was stirred for 30 minutes and extracted twice with diethylether. The extracts were washed with water and brine, and the solution was dried (MgSO$_4$). The solvent was removed under vacuum to leave a yellow oil (26.79 g). Purification by flash chromatography (230–400 mesh silica gel, 50% ethyl acetate in hexane to pure ethyl acetate) gave the title compound as a yellow oil (B-6, 6.76 g, 36%). NMR (CDCl$_3$, TMS)δ1.3–1.45 (m, 1H), 1.45–1.6 (broad,2H,NH and OH), 1.6–1.77 (m,3H), 1.77–1.91 (m, 1H), 1.91–2.05 (m, 1H), 2.65–2.78 (m,1H), 2.85–2.98 (m,7 lines, 1H), 3.04 (d,J=10.5 Hz, 1H), 3.12 (m,1H), 3.62 (m,2H), 3.828 (AB,J=13.3 Hz,N-CH$_2$,2H), 6.92–7.04 (m,2H), 7.20–7.39 (m,6H). IR (Major peaks) 3585, 3319, 3084, 3059, 3026, 1602, 1586, 1559, 1495, 1453, 1437, 1131, 1062, 1028, 773, 747, 730, 699. Mass spec. m+ at m/z 373, 375.

Preparation 12:
Trans-8-bromo-1,2,3,4-tetrahydro-2-(3-bromopropyl)-1-[(phenylmethyl)amino]naphthanene and trans-1,2,3,4,4a,5,6,10b-octahydro-10-bromo-4-(methylhenyl)benzo[f]quinoline (B-7,8, Chart B)

A mixture of trans-8-bromo-1,2,3,4-tetrahydro-2-(3-hydroxypropyl)-1-[(phenylmethyl)amino]naphthalene (B-6, 1.8 g, 4.8 mmol) and 48% hydrobromic acid (20 mls) was stirred at reflux in an oil bath maintained at 100° C. for 3 hours. The excess hydrobromic acid was removed under vacuum to leave B-7 as the hydrobromide salt. Potassium carbonate (3.0 g, 22 mmol) and acetonitrile (40 mls) were added, and the mixture was stirred at reflux for 22 hours. The mixture was diluted with water and extracted twice with diethylether. The extracts were washed with brine and dried (MgSO$_4$). The solvent was removed under vacuum to leave a brown oil (1.65 g). Purification by flash chromatography (230–400 mesh silica gel; 5% ethyl acetate in hexane) gave a light-yellow oil (1.15 g, 67%). The compound was dissolved in diethylether, and excess ethereal HCl was added. The precipitate was centrifuged, washed with diethylether, and crystallized from methanol/diethylether to give the title compound as a colorless solid B-8, 1.12 g, m.p. 242°–243° C.

Resolution of the amine (B-8): The amine free base (4.64 g, 0.0130 mol) was mixed with di-p-toluoyl-L-tartaric acid monohydrate (5.27 g, 0.0130 mol), and the mixture was crystallized twice from methanol to give colorless crystals (2.88 g). The compound was released to the free base by partitioning between diethylether and dilute ammonium llydroxide to give a colorless oil: 1.16 g, $[\alpha]_D$=+100.6° (25° C., THF, C=1.03).

The combined filtrates were evaporated under vacuum, and the residue was released to the free base by partitioning between diethylether and dilute ammonium hydroxide. The resulting amber oil (3.26 g, 9.15 mmol) was combined with di-p-toluoyl-D-tartaric acid (3.54 g, 9.16 mmol), and the mixture was crystallized twice from methanol leaving a colorless solid (2.68 g). The compound was released to the free base by partitioning between diethylether and dilute ammonium hydroxide leaving the title compound as a colorless oil: 1.11 g, $[\alpha]_D=102.1°$ (25° C., THF, C=1.03).

Preparation 13:
trans-1,2,3,4,4a,5,6,10b-octahydro-10-(aminocarbonyl)-4-(methylphenyl)benzo[f]quinoline (B-9, Chart B)

A solution of the (−)-trans-1,2,3,4,4a,5,6,10b-octahydro-10-bromo-4-(methylphenyl)benzo[f]quinoline (B-8, 6.60 g, 18.5 mmol) in dry tetrahydrofuran (50 mls) under nitrogen was cooled to −78° C., and t-bulyllithium (1.7M in pentane, 22.3 mls, 38.1 mmol) was added in about 10 seconds. The mixture was stirred at −78° C. for 5 minutes, and trimethylsilylisocyanate (46.5 mmol) was added via a syringe in one shot. The cold bath was removed, and the mixture was stiffed at ambient temperature for 1.5 hours. Water (30 mls) was added, and the mixture was stiffed for 10 minutes. Hydrochloiric acid (10%, 10 mls) was added, and file mixture was stiffed for 30 minutes. The mixture was bascified with 15% NaOH and extracted 3 times with methylene chloride. The extracts were dried (MgSO$_4$), and the solvent was removed under vacuum to leave a white solid containing solvent (10.76 g). A sample (0.52 g) was crystallized from acetonitrile (20 mls) to yield the title compound (−) B-9 as white crystals (0.21 g, m.p. 189°–190° C., $[\alpha]_D=-183.7°$ (25° C., THF, C=0.705)).

The (+)-amide (+) B-9 was prepared in a manner similar to that for the (−) B-9 above using (+) B-8 as the starting material. (m.p. 185°–186° C.$[\alpha]_D=+189.5°$ (25° C., THF, C=0.695)).

The racemic B-9 was prepared in a manner similar to that for (−) B-9 above using racemic B-9 as the starting material. (m.p. 182°–183.5° C).

Preparation 14:
trans-1,2,3,4,4a,5,6,10b-octahydro-10-(aminocarbonyl)benzo[f]quinoline (B-10, Chart B)

A mixture of trans-1,2,3,4,4a,5,6,10b-octahydro-10-carboxamido-4-(methylphenyl)benzo[f]quinoline as a solvate (B-9, 10.2 g, ~18.5 mmol), Pearlman's catalyst (20% palladium hydroxide on carbon, 1.0 g), and ethanol (200 mls) was shaken in a Parr apparatus for 18.5 hours using an initial hydrogen pressure of 48 psi. The mixture was filtered through celite, and the filtrate was evaporated leaving a solid (5.4 g). The mixture was partitioned between 1:1 tetrahydrofuran/diethylether and 10% sodium carbonate (30 mls). The aqueous solution was saturated with sodium chloride and extracted again with 1:1 tetrahydrofuran/diethylether. The combined extracts were washed with brine and dried (MgSO$_4$). The solvent was removed under vacuum to leave a white solid (4.15 g). A sample was crystallized from acetonitrile to yield the title compound (−) B-10 as yellow crystals (m.p. 208°–214° C.). $[\alpha]_D=-298.0°$ (25° C., CH$_3$OH, c=0.725).

The trans-(+)-1,2,3,4,4a,5,6,10b-octahydro-10-carboxamido-benzo[f]quinoline((+)-B-10) was prepared using a procedure similar to that for (−) isomer of B-10 using the (+)B-9 as the starting material: m.p. 192.5° C., $[\alpha]_D=+378.7°$ (25° C., THF, c=0.475).

The racemic B-10 was prepared using a procedure similar to that for the (−) isomer using racemic B-9 as the starting material. NMR (CDCl$_3$, TMS)δ1.00 (q of d, 1H), 1.40–1.70 (m,3H), 1.77 (m,1H), 2.38 (br. q,2H), 2.61 (t of d, 1H), 2.672 (d of d, 1H), 2.87 (br. t,2H), 2.98 (m,1H), 3.35–3.55 (br. s, 6H,OH/NH), 7.095 (m,3H), 7.295 (s,1H), 7.781 (s, 1H).

Preparation 15:
(±)-1,2,3,4-Tetrahydro-8-bromo-2-oxo-1-naphthalene Acetic acid Methyl Ester (C-2, Chart C)

An oven-dried, 5 L, 3-neck flask, equipped with a dropping funnel and a mechanical stirrer was charged with 3 (71.73 g, 0.32 mol) and THF (2 L). The flask was cooled to −30° C. and LDA (1.5M, 234 mL, 0.35 mol) was added slowly over a 30 min period. Stirring was continued for 30 min more after addition was completed. Methyl bromoacetate (36.2 mL, 0.382 mol) in 500 mL THF was added slowly over 45 min and the dark brown solution was stirred for 4 h. The reaction was quenched with concentrated HCL(55 mL) to pH<3. The solvent was removed in vacuo and the concentrate was extracted with ethyl acetate (2 L). The organic layer were washed with water, brine, dried (MgSO$_4$), filtered and concentrated to give a dark brown oil. This oil was plurified by flash chromatography on 1kg of silica gel, elutingfirst with hexane followed by 15% ethyl acetate/hexane, and collecting 400 mL fractions. Fractions 14–25 were combined and concentrated in vacuo to give 4 as a brown oil (78 g, 82%).d.$^1$H NMR (CDCl$_3$): δ 7.48 (d, J=7.8 Hz, 1H), 7.18 (d, J=7.8 HZ, 1H), 7.09 (t, J=7.8 Hz, 1H), 3.97 (t,J=5.4 Hz, 1H), 3.60 (s, 3H), 3.57–3.45 (m, 1H), 3.31–3.24 (m, 1H), 3.09–2.91 m,2H), 2.84–2.77 (m, 1H), 2.61–2.49 (m, 1H. IR (mull); $v_{max}$ 1742, 1712, 1595, and 1563 cm$^{-1}$. MS: M$^+$ 296, other ions at m/z 265, 236, 223, 217, 195, 175, 157, 144, 129, 115. Analysis: Calcd for C$_{13}$H$_{13}$BrO$_3$: C, 52.55; H, 4.41.

Found: C, 52.61; H, 4.45. TLC: R$_f$=0.37 eluted with hexane/ethyl acetate (4:1).

Preparation 16: [4bS-(4b.alpha., 8.beta., 10aR*)]-4-bromo-4b,5,8,9,11,12-hexahydro-8-phenyl-6H-Benz[e]oxazolo[2,3-i]indol-6-one (C-3, Chart C)

A 1-L round bottom flask was charged with keto-ester C-2 (29.18 g, 0.098 mol), toluene (490 mL), and (R)-2 -phenylglycinol (20.21 g, 0.147 mol) and fitted with a Dean-Stark trap. The reaction suspension was heated to reflux, and after approximately 1 hour the reaction became homogenous. Heating was continued for 18 hours, by which time the trap contained ca. 2.0 mL of water (theory=1.8 mL). The reaction mixture was cooled to RT and concentrated in vacuo. The crude product thus obtained was purified by chromatography on the Prep 500 using 20% ethyl acetate/hexane to give 34.75 g (92%) of C-3 as a pale yellow solid, mp 123.0°–125.5°; R$_f$ 0.24(20% ethyl acetate/hexane); IR (mull) 2949, 2926, 2855, 1710, 1447, 1364, 1025, 786, 718, 702 cm$^{-1}$; $^1$H NMR (300 MHz, CDCl$_3$) 7.37 (m,6H, aromatic), 7.12 d, J=6.7 Hz, 1H, aromatic), 7.05 (t,J=7.6 Hz, 1H, aromatic), 5.33 (t,J=7.3 Hz, 1H, N—CH), 4.70 (dd, J=8.7, 8.1 Hz, 1H, O—CH$_{2a}$), 4.23 (dd, J=8.8, 6.6 Hz, 1H, O—CH$_{2b}$), 3.84 (t, J=9.8, 1H, Ph—CH$_{r}$), 3.51 (dd,J−17.1, 9.5 Hz, 1H, O=C—CH$_{2a}$), 2.84 (t,J=6.0 Hz, 2H, Ph—CH$_2$), 2.57 (dd, J=17.1, 10.3 Hz, 1H, O=C—CH$_{2b}$), 2.09 (2.09 (m, 1H, Ph—C(H)$_2$, 1.85 (m, 1H, Ph—C(H)$_2$—CH$_{2b}$); $^{13}$C NMR (75.5 MHz, CDCl$_3$) 176.9, 139.8,138.7,136.3,131.2, 128.8,128.1,127.6,125.5,124.7,101.2, 73.4,57.5,44.9,41.1,30.7,27.3, $[\alpha]_D$−265° (c 0.961, methanol). Anal. Calcd for C$_{20}$H$_{18}$N$_1$O$_2$Br$_1$: C,62.51; H, 4.72; N, 3.65. Found: C, 62.55; H, 4.76; N, 3.61.

Preparation 17:
cis-(±)-2,3,3a,4,5,9b-hexahydro-9-bromo-3-(2-R-hydroxymethylbenzyl)-1H-benz[e]indole (C-4, Chart C)

a) Borane method: A solution of lactam C-3 (0.769 g, 2.00 mmol) in anhydrous THF (10 mL) was cooled to −78° C. and treated dropwise with a 1M solution of borane in THF (6.0 mL, 6.00 mmol). The reaction was stirred for 2 hours at −78, then for 2 hours at RT, then finally brought to reflux for 3 hours. After stirring at RT overnight, the reaction was treated dropwise with 1M aqueous HCl (5 mL), causing vigorous gas evolution. The reaction was again brought to reflux for an hour, then cooled RT and poured into brine (30 mL). The aqueous phase was basified to pH 10 with 5N NaOH and extracted with dichloromethane (3×30 mL). The combined organic phases were dried over MgSO$_4$, filtered, and concentrated to a colorless oil. The crude product thus obtained was purified by flash chromtography on 60 g silica gel using 20% ethyl acetate/hexane to give 692 mg (93%) of C-4 as a colorless tacky solid: R$_f$ 0.20 (15% ethyl acetate/hexane); IR (neat) 2936, 1453, 1442, 1177, 1081, 1060, 1035, 1029, 767, 703 cm$^{-1}$; $^1$H NMR (300 MHz, CDCl$_3$) 7.36 (m, 4H, aromatic), 7.23 (m, 2H, aromatic), 7.05 (d, J=7.4 Hz, 1H, aromatic), 6.69 (t, J=7.7 Hz. 1H, aromatic). 4.07 (m, 2H, N—CH—Ph & O—CH$_2$a), 3.69 (dd, J=9.2, 4.1 Hz, 1H, O—CH$_{2b}$), 3.42 (dd, J=18.4, 9.1 Hz, 1H, Ph—CH$_{rj}$), 3.10 (m, 2H, OH & N—CH$_{rj}$), 2.95 (t, J=7.8 Hz, 1H, N—CH$_{2a}$), 2.79 (m, 1H, Ph—CH$_{2a}$), 2.51 (m, 2H, Ph—CH$_{2b}$ & N—C(H)$_2$—CH$_{2a}$), 2.30 (m, 1H, N—CH$_{2b}$), 2.18 (d of q, J=13.7, 3.5 Hz, 1H, N—C(H)—CH$_{2a}$), 1.48 (m, 1H, N—C(H)—CH$_{2b}$), 1.33 (m, 1H, N—C(H)$_2$—CH$_{2b}$), $^{13}$C NMR (75.5 MHz, CDCl$_3$) 140.2, 139.4, 134.7, 130.3, 129.2. 128.0, 127.7, 127.3, 126.5, 124.5, 62.7, 61.1, 56.4, 44.6, 41.0, 31.6, 26.0, 25.9; [α]$_D$−127° (c 0.566, methanol). Anal. Calcd for C$_{20}$H$_{22}$H$_1$O$_1$Br$_1$ ·0.5 H$_2$O: C, 63.00; H, 6.08; N, 3.67. Found: C, 63.02; H, 5.83; N, 3.60.

b) DIBAL method: To a cold (−78° C.) solution of diisobutylaluminum hydride (25 mL, 1M in toluene, 25 mmol) in anhydrous THF (100 naL) was added dropwise over 15 min a solution of C-3 (1.92g, 5.0 mmol) in THF (50 mL). The reaction was allowed to stir overnight with gradual expiration of the cooling bath. The clear, colorless reaction mixture was then quenched by the addition of methanol (10 mL) and stirred at RT until gas evolution had ceased. The reaction was diluted with dichloromethane (250 mL) and treated with an aqueous solution of Na/K-tartrate (0.3 M, 100 mL). The resulting two-phase mixture was stirred vigorously for 30 min, at which point the layers were separated and the aqueous phase was extracted with CH$_2$Cl$_2$ (2×100 mL). The combined organic phases were washed with brine (200 mL), dried over MgSO$_4$, filtered, and concentrated in vacuo. This material was purified by chromatography on silica gel (140 g) using 15% ethyl acetate/hexane to give 1.65 g (89%) of C-4 as a colorless oil.

c) Alane method: To a cold (−78° C.) solution of lithium aluminum hydride (30 mL, 1M in THF, 30 mmol) in anhydrous THF (80 mL) was carefully added aluminum(III) chloride (4.00 g, 30 mmol) in several portions. After stirring for 10 min at −78° C., the resulting white suspension was treated dropwise with a solution of C-3 (2.31 g, 6.0 mmol) in THF (40 mL) and stirring was continued for 1 hr at −78° C. The reaction was allowed to warm to RT, then treated sequentially with water (1.1 mL), 5N NaOH (1.0 mL), and water again (4.0 mL). The resulting suspension was poured into 1 N NaOH (200 mL) and extracted with dichloromethane (2×300 mL). The combined organic phases were washed with brine (200 mL), dried over MgSO$_4$, filtered, and concentrated to an oil. This is material was purified by chromatography on silica gel (200 g) using 20% ethyl acetate/hexane to give 1.70 g (76%) of C-4 as a slightly yellow tacky solid.

Preparation 18:
cis-(±)-2,3,3a,4,5,9b-hexahydro-9-bromo-3-(2-R-benzyloxymethylbenzyl)-1H-benz[e]indole (C-5, Chart C)

To a solution of amino-alcohol C-4 (16.5g, 44.3 mmol) in anhydrous DMSO (148 mL) was added freshly-powdered potassium hydroxide (11.71 g of 85% material, 0.18 mol), resulting in an immediate dark-orange reaction mixture. The reaction was stirred at RT for 10 min prior to the dropwise addition of benzyl chloride (10.2 mL, 88.7 mmol). The reaction was stirred for an additional 50 min. during which time the reaction color gradually changed to yellow. At this point, the reaction was added to ice water (300 mL), and the resulting milky aqueous suspension was extracted with dichloromethane (3×400 mL). The combined organic phases were washed once with brine (300 mL), dried over MgSO$_4$, filtered, and concentrated to give 21.17 g of a yellow syrup. This crude product was purified by chromatography on the Prep 500 using 5% ethyl acetate/hexane to give 16.99 g (83%) of C-5 as a pale yellow syrup: R$_f$0.28 (5% ethyl acetate/hexane); IR (mull) 2966, 2944, 2924, 2888, 2861, 2807 1453, 1110, 734, 695 cm$^{-1}$: $^1$H NMR (300 MHz, CDCl$_3$) 7.28 (m, 11H, aromatic), 7.01 (d, J=7.4 Hz, 1H, aromatic), 6.92 (t, J=7.7 Hz, 1H, aromatic), 4.50 (dd, J=15.7, 12.2 Hz, 2H, Ph—CH$_2$—O), 4.07 (t, J=6.3 Hz, 1H, N—CH—Ph), 3.87 (dd, J=9.7, 6.1 Hz, 1H, Ph—C(H)—CH$_{2a}$), 3.77 (dd, J=9.7, 6.6 Hz, 1H, Ph—C(H)—CH$_{2b}$), 3.40 (q, J=8.4 Hz, Ph—CH$_{rj}$), 3.07 (m, 1H, N'2.56 (m, 3H, Ph—CH$_{2b}$ & N—C(H)$_2$—CH$_{2a}$), 1.93 (m, 1H, N—C(H)—CH$_{2a}$), 1.53 (m, 1H, N—C(H)—CH$_{2b}$), 1.38 (m, 1H, N—C(H)$_2$—CH$_{2b}$); $^{13}$C NMR (75.5 MHz, CDCl$_3$) 140.4, 139.9, 138.7, 138.4, 130.4, 128.8, 128.3, 128.0. 127.5, 127.4, 127.2, 126.2, 125.0, 73.2, 73.1, 63.8, 58.0, 47.9, 41.7, 31.4, 27.3, 24.8; [α]$_D$−92° (c 0.9895, methanol). Anal. Calcd for C$_{27}$H$_{28}$N$_1$O$_1$Br$_1$: C, 70.13; H, 6.10; N, 3.03. Found: C, 69.94; H, 6.01; N, 2.87.

Preparation 19:
cis-(±)-2,3,3a,4,5,9b-hexahydro-9-bromo-1H-benz[e]indole (C-6, Chart C)

A solution of benzyl ether C-5 (16.96 g, 36.7 mmol) in chlorobenzene (70 mL) was treated with 1-chloroethyl chloroformate (20.0 mL, 0.183 mol) and healed to reflux (bath temp 150° C.). During the initial minutes of heating the reaction darkened to deep emerald green. After 18 hours at reflux, the now-brown reaction mixture was cooled to RT and treated with a second portion of the chloroformate reagent (20 mL) and refluxing was continued for an additional 4 hours. The reaction was then cooled, treated with methanol (500 ml), and re-heated to reflux for 1 hour. At this point, the reaction was cooled to RT and concentrated to a brown oil. This material was dissolved in dichlormethane (300 mL) and washed 3 times with 1M hydrochloric acid (aq). The combined aqueous acidic washes were cooled in an ice bath and adjusted to pH>13 with 50% sodium hydroxide, forming a milky solution. This basic aqueous phase was extracted with dichloromethane (2×600 mL) and the combined organic layers were dried over MgSO$_4$, filtered, concentrated in vacuo to give 7.91 g (86%) of C-6 as a light tan oil. This material was earned on without further purification: IR (neat) 2961, 2934, 2862, 2841, 1560, 1453, 1440, 1400, 1176, 774 cm$^{-1}$; $^1$H NMR (300 MHz, CDCl$_3$) 300 MHz, CDCl$_3$) 7.40 (d, J=7.7 Hz, 1H, aromatic), 7.05 (d, J=7.3 Hz, 1H, aromatic), 6.95 (t, J=7.7 Hz, 1H, aromatic), 3.51 (m, 2H, N—CH & Ph—CH), 3.06 (m, 1H, N—CH$_{2a}$), 2.92 (m, 1H, N—CH$_{2b}$), 2.76 (m, 1H, Ph—CH$_{2a}$), 2.65 (m, 2H, Ph—CH$_{2b}$ & Ph—C(H)—CH$_{2a}$), 2.23 (bs, 1H, NH), 1.80 (m, 1H, N—C(H)—CH$_{2a}$), 1.65 (m, 1H, N—C(H)—CH$_{2b}$), 1.41 (m, 1H, Ph—C(H)—CH$_{2b}$); $^{13}$C NMR (75.5 MHz, CDCl$_3$) 3139.8, 139.5, 130.6, 127.7, 126.8, 125.6, 56.2, 45.3, 42.6, 33.8, 28.4, 27.3; [α]–113° (c 0.6461, methanol).

Preparation 20:
cis-(±)-2,3,3a,4,5,9b-hexahydro-9-bromo-3-(n-propyl)-1H-benz[e]indole (C-7, Chart C)

A solution of the secondary amine C-6 (7.34 g, 29.0 mmol) in propionic acid (50 mL) was heated to 50° C. under nitrogen. To this light tan reaction mixture was added sodium borohydride (5.07 g. 0.134 mol) in five equal portions over a period of 15 minutes. The addition of the borohydride reagent was accompanied by a vigorous foaming and a lightening in reaction color. After stirring overnight at 50° C., the reaction was cooled to RT, quenched with 10% aqueous NaOH (300 mL), and extracted with dichloromethane (3×500 mL). The combined organic phases were washed once with brine (300 mL), dried over MgSO$_4$, filtered, and concentrated to give 10.63 g of a yellow oil. This oil was purified by chromatography on a Prep 500 using 15% ethyl acetate/hexane to give 7.38 g (86%) of C-7 as a pale yellow mobile oil: R$_f$ 0.32 (15% ethyl acetate/hexane); $^1$H NMR (300 MHz, CDCl$_3$) 7.36 (m, 1H, aromatic), 7.02 (d, J=7.4 Hz, 1H, aromatic), 6.93 (t, J=7.6 Hz, 1H, aromatic), 3.57 (q, J=9.1 Hz, 1H, Ph—CH), 3.07 (t, J=8.2 Hz, 1H, N—CH$_{2ar}$), 2.88 (m, 1H, Ph—CH$_{2a}$) 2.76–2.66 (m, 3H, N—CH & N—CH$_{2ac}$ & Ph—C(H)—CH$_{2a}$), 2.53 (m, 1H, Ph—CH$_{2b}$), 2.20 (m, 2H, N—CH$_{2br}$ & N—CH$_{2bc}$), 1.90 (m, 1H, N—C(H)—CH$_{2a}$), 1.49 (m, 4H, C(H)$_3$—CH$_2$ & N—C(H)—CH$_{2b}$ & Ph—C(H)—CH$_{2b}$, 0.95 (t, J=7.1 Hz, 3H, CH$_3$); $^{13}$C NMR (75.5 MHz, CDCl$_3$) 140.9, 140.1, 130.4, 127.5, 126.6, 124.9, 62.3, 56.3, 52.5, 41.8, 32.5, 26.4, 21.8, 12.1.

Preparation 21:
cis-(±)-2,3,3a,4,5,9b-hexahydro-9-carboxamido-3-(n-propyl)-1H-benz[e]indole (C-8, Chart C)

A solution of t-BuLi (2.5 mL, 1.7 M in pentane, 4.2 mmol) was added dropwise to a pre-cooled flask (–78° C.) containing anhydrous THF (6 mL). To the resulting mixture was added a solution of C-7 (0.59 g, 2.0 mmol) in THF (3 mL) over a period of 5 min. The yellow reaction mixture was stirred at –78° C. for an additional 10 min and then quickly treated with freshly-distilled trimethylsilyl isocyante (0.41 mL, 3.0 mmol). Stirring was continued for 1.5 hours, then warmed to RT and quenched with saturated aqueous NH$_4$Cl solution (25 mL). Volatiles were removed in vacuo and the resulting aqueous phase was adjusted to pH>13 with 20% NaOH. The basic phase was extracted with ethyl acetate (3×25 mL) and the combined organic layers were washed with brine, dried over MgSO$_4$, filtered, and concentrated. The residue thus obtained was purified by chromatography on silica gel (25 g) using 50% acetone/hexane to give 0.41 g (79%) of C-8, [α]$_D$=–227°.

Preparation 22:
cis-2,3,3a,4,5,9b-hexahydro-9-carboxamido-3-[2-(R)-hydroxymethylbenzyl)-1H-benz[e]indole (D-2, Chart D)

Cis-2.3,3a,4,5,9b-hexahydro-9-bromo-3-[2-(R)-hydroxymethylbenzyl)-1H-benz[e]indole (D-1, Chart D) (69 g, 185.5 mmol) was placed in a one liter 3-neck round bottom flask fitted with a reflux condensor and gas inlet tube (not a sintered glass tube) with palladium acetate (2.08 g, 0.05 eq.) and 1,3-bis-diphenylphosphinopropane (dppp) (4.60 g, 0.06 eq.) and flushed with nitrogen. DMF (190 ml), hexamethyldisilylane (274 ml, 7 eq.), and diisopropylethylamine (65 ml. 2 eq.), all from freshly opened bottles, were added. Carbon monoxide was introduced via the gas inlet tube and allowed to flush the slurry for 10 min. The slurry was heated on a steam bath to 100° and allowed to stir vigorously. The carbon monoxide bubble rate was adjusted with the aid of a mineral oil bubbler attached to the top of the reflux condensor. The gas was allowed to just barely give rise to noticible bubbles.

After stirring 16 hr, the dark solution was cooled and methylene chloride (400 ml) and ether (800 ml) was addded. This was extracted with 150 ml 2N sodium hydroxide dissolved in water (1000 ml). The organic layer was washed with water (3×500 ml). The solvent was removed (attempting to remove most of the diisopropylethylamine) to afford a black syrup. This was redissolved in methylene chloride (300 ml) and 2 N aqueous hydrochloric acid was added (300 ml) while swirling. Water (600 ml) was added followed by the slow addition of ether (1000 ml) while swirling. After extraction the aqueous layer was set aside. The organic layer was back-extracted with water (500 ml). The aqueous layers were combined and methylene chloride (400 ml) was added, followed by 3N aqueous sodium hydroxide (250 ml) with swirling. Ether (1000 ml) was added and the mixture was shaken vigorously and the layers separated. The organic layer was washed with water (500 ml) and brine, dried over sodium sulfate, and the solvent removed in vacuo to afford a light brown foam (59.8 g). This was filtered through a plug of flash silica gel (230–400 mesh) with ethyl acetate/hexane (85:15), switching to neat ethyl acetate. Solvent removal afforded an almost white foam (55.8 g, 166 mmol, 89.5%), m.p. 80°. $^1$H NMR (300 MHz, CDCl$_3$): 7.4–7.18 (m, 7H), 7.11 (t, 1H, J=7.8), 5.76 (BS, 2H), 4.10–3.97 (m, 2H), 3.76–3.65 (m, 2H), 3.23 (m, 1H), 3.13 (dt, 1H, J=9, 3), 2.93–2.80 (m, 2H), 2.59 (dt, 1H, J=15.1, 3), 2.36–2.24 (m, 2H), 2.15–2.10 (m, 1H), 1.56–1.38 m, 2H).$^{13}$C NMR (75 MHz, CDCl$_3$): 172.6 (q), 139.5 (q), 138.3 (q), 135.0 (q), 134.9 (q), 130.2 (t), 129.3 (t), 128.1 (t), 127.8 (t), 125.1 (t), 124.7 (t), 63.0 (t), 61.1 (d), 56.3 (t), 44.8 (d), 37.8 (t), 33.9 (d), 26.7 (d), 26.2 (d). IR (mull): 3600, 3050, 2980, 1660, 1600, 1436, 1378 cm$^{-1}$. MS (70 EV, m/e): 429(M$^+$), 306, 305, 260, 216.

Preparation 23:
cis-2,3,3a,4,5,9b-hexahydro-9-carboxamido-1H-benz[e]indole (D-3, Chart D)

Because of space limitations in the Parr bottle, the hydrogenolysis reactions were carried out in two roughly equal-size portions (total of 55.8 g, 166 mmol). Carboxamide D-2 (Chart D) (27.6 g, 82.14 mmol), 20% palladium hydroxide on carbon (6.7 g), and absolute ethanol (150 ml) were placed in a Parr hydrogenation bottle and fitted with a thermostated heating mantle. The slurry was hydrogenated for 16 at 50° and 45 p.s.i. After cooling, the slurry was filtered with the aid of diamataceous earth and rinsed with methanol. The solvent was removed in vacuo to afford a viscous oil, consisting of D-3 and 2-phenylethanol, which partially solidified upon standing. These two lots were combined and carried onto the next step without purification. An analytical sample was crystallized from ethanol (m.p. 189°). $^1$H NMR (300 mHz, MeOD): 7.25–7.11 (m, 3H), 3.82 (dd, 1H, J=18.3, 8.4), 3.52 (m, 1H), 3.04–2.97 (m, 1H), 2.89–2.70(m, 4H), 2.47–2.38 (m, 1H), 1.79–1.71 (m, 2H), 1.59–1.46 (m, 1H). IR (mull): 3400, 3195, 2960, 1640, 1630, 1609, 1582, 1455, 1390, 1100 cm$^{-1}$. MS (70 EV, m/e): 216(M$^+$), 198, 187, 170, 156, 143, 128.

Preparation 24:
cis-2,3,3a,4,5,9b-hexahydro-9-carboxamido-3-n-propyl-1H-benz[e]indole (D-4, Chart D)

Crude secondary amine D-3 (Chart D) (166 mmol, based on the starting mount of carboxamide D-2 (Chart D) used in Preparation 22, was mixed with anhydrous sodium carbonate (21 g, 1.2 eq.), n-bromopropane (75 ml, 5 eq.), acetonitrile (275 ml), and DMF (55 ml) and heated to 80° for 14 hr. The 2° amine goes into solution slowly. After cooling, the slurry was placed in a separatory funnel with ether (500 ml) and methylene chloride (50 ml) and washed with water (2×500 ml). To the organic layer was added 2N aqueous hydrochloric acid (150 ml) and water 250 ml) and shaken vigorously. The aqueous layer was set aside and the organic layer again extracted with water (250 ml). The aqueous layers were combined and extracted with ether (300 ml). 2N aqueous sodium hydroxide (175 ml) was added to the aqueous layer followed by ether (400 ml) and methylene chloride (150 ml). This was extracted and the organic layer washed with water (200 ml) and brine. Drying over sodium sulfate and removal of solvent in vacuo afforded an off white solid which is identical to authentic U-93385 (32.1 g, 124 mmol) (M.P.=165°). A yield of 75% for the last two steps and a 67% overall yield from D-1 (Chart D). $^1$H NMR (300 mHz, CDCl$_3$): 7.26–7.10 (m, 3H), 5.74 (bs, 2H), 3.92 (dd, 1H, J=18.5, 7), 3.09 (m, 1H), 2.91–2.65 (m, 3H), 2.59–2.4 (m, 4H), 1.92 (m, 1H), 1.65–1.4 (m, 4H), 0.93 (t, 3H, J=7).

Preparation of maleic acid salt of D-4

The freebase of D-4 (Chart D) (50.7 g, 196.5 mmol) was dissolved in methanol and warmed. To this was added a hot methanolic solution of maleic acid (23.94 g, 1.05 eq.). While stirring, ether was added to cause crystallization. After cooling, a first crop was obtained (69 g) (M.P.=216°). Only two peaks were seen in the reversed phase HPLC trace using gradient elution, maleic acid (1.48 min) and U983385 (4.63). HPLC conditions: 15 ml/min gradient (2 ml/min flow) beginning at 10% acetonitrile/pH 3 (phosphate buffer) water and going to 85 % acetonitrile/pH 3 water, using a 3.9×300 mm Bond-Pac C-18 column with detection at 215 nm.

Preparation 25: [4bS-(4b.alpha.,8.beta., 10aR*)]-4-bromo-4b,5,8,9,11,12-hexahydro-5-methyl-8-phenyl-6H-Benz[e]oxazolo[2,3-i]indol-6-one (E-2, Chart E)

A solution of E-1 (7.69 g) in THF (40 mL) was cooled to −78° C. and treated dropwise with a 1M solution of lithium bis(trimethylsilyl)amide in THF (22 mL). After stirring at −78° C. for 1h, the reaction was treated with iodomethane (3.75 mL) and the reaction was stirred for 16h with gradual warming to RT. The reaction was added to a saturated aqueous NH$_4$Cl solution (120 mL) and volatiles were removed in vacuo. The remaining aqueous phase was acidified to pH<2 with 1N HCl and extracted three times with dichloromethane. The combined organic layers were washed with brine, dried over MgSO$_4$, filtered, and concentrated. The product was purified by silica gel chromatography using 10% ethyl acetate/hexane to give 7.63 g (96% yield) of E-2 (R1=Me). 1H NMR (CDCl$_3$, 300 MHz) δ7.50–7.03 (m, 8H, aromatics), 5.35 (t, 1H, J=7.2 Hz, N—CH), 4.73 (t, 1H, J=8.1 Hz, O—CH), 4.16 (t, 1H, J=8.1 Hz, O—CH), 3.84 (d, 1H, J=9.7 Hz, Ph—CH), 2.85–2.68 (m, 3H, Me—CH, Ph—CH$_2$), 2.25 (dt, 1H, J=9.7, 3.1 Hz, —CH$_2$—), 1.51 (dt, 1H, J=3.1, 9.7 Hz,—CH$_2$-), 1.42 (d, 3H, J=7.6 Hz,—CH$_3$); 13C NMR (CDCl$_3$, 75.5 MHz) δ 6 179.6, 140.7, 140.0, 137.2, 131.4, 128.8, 128.1, 127.5, 127.4, 125.4, 124.2, 100.9, 72.8, 57.1, 52.3, 48.8, 33.4, 27.2, 15.6; Anal. calcd for C21H20N1O2Br1: C, 63.33; H, 5.06; N, 3.52. Found: C, 63.13; H, 5.04; N, 3.48.

Preparation 26:
cis-(±)-2,3,3a,4,5,9b-hexahydro-9-bromo-3-(2-R-hydroxymethylbenzyl)-3a-(3-propenyl)-1H-benz[e]indole (E-3, Chart E)

A solution of E-1 (7.69 g) and allyltrimethylsilane (7.0 mL) in dichloromethane (200 mL) was cooled to −78° C. and treated with titanium tetrachloride (4.8 mL). The cooling bath was removed and the reaction was allowed to warm to room temperature over 1h. The reaction was then quenched with saturated aqueous NH$_4$Cl solution and volatiles were removed in vacuo. The resulting aqueous layer was extracted four times with dichloromethane, and the combined organic layers were washed with brine, dried over MgSO4, filtered, and concentrated. The product was purified by silica gel chromatography using 20% acetone/hexane to give E-3 (7.78 g, 91% yield, R1=allyl) as a white solid, mp 156.5–157.5; 1H NMR (CDCl$_3$, 300 MHz) δ7.47–7.26 (m, 6H), 7.11–6.99 (m, 2H), 5.32–5.21 (m, 1H), 4.91 (d, 1H, J=20.5 Hz), 4.86 (d, 1H, J=23.4 Hz), 4.48–4.34 (m, 2H), 4.14 (dd, 1H, J=7.4, 1.5 Hz), 4.04–3.98 (m, 1H), 3.71 (dd, 1H, J=9.2, 7.4 Hz), 3.22 (dd, 1H, J=20.1, 9.4 Hz), 2.91 (m, 1H), 2.75–2.60 (m, 1H), 2.25–2.02 (m, 4H), 1.84–1.69 (m, 1H); 13C NMR (CDCl$_3$, 75.5 MHz) δ 176.6, 139.0, 138.8, 137.3, 131.8, 131.2, 128.6, 127.9, 127.7, 125.0, 120.0, 67.9, 65.3, 60.7, 43.3, 40.6, 38.6, 30.2, 26.3; Anal. calcd for C23H24N 1 O2Br1: C, 64.80; H, 5.67; N, 3.29. Found: C, 64.62; H, 5.61; N, 3.22.

EXAMPLE 1 cis-(±)-2,3,3a,4,5,9b-hexahydro-9-carboxamido-3-(n-propyl)-1H-benz[e]indole (A-8, Chart A)

A solution of 1.9 g (6.95 mmol) cis-(±)-2,3,3a,4,5,9b-hexahydro-9-carbomethoxy-3-(n-propyl-1H-benz[e]indole (A-7) (racemic), 2 mL 12.75 N NaOH, 2 mL water and 10 mL methanol was refluxed overnight (bath temp 70–80 C.). TLC showed no sm was present. The mixture was neutralized with 6N HCl (to pH 5). The solution was concentrated to dryness using methanol and toluene. A light yellow solid was recovered. A solution of this solid in 40 mL DMF and 2.9 mL triethylamine was flushed with ammonia (gas) (bubbled through) for 10 min, treated with 2.25 mL (13.90 mmol) diethylcyanophosphonate, and then stirred overnight with ammonia bubbling through. Direct spot TLC showed no sm remaining. The reaction mixture was concentrated in vacuo to a solid and dissolved in methanol. This solution was flash chromatographed on 400 g silica gel 60 (230–400 mesh) eluting first with hexane/ethyl acetate (1:1) to remove the non-polar impurities. Then using methylene chloride/methanol with 2.2.5 M NH$_3$ (95:5). Homogeneous fractions were combined and concentrated to yield the title compound as a white solid. The solid was recrystallized using acetone to yield a white solid (A-8, 1.46 g, 81.5%): mp 149° C.1HNMR (CDCl$_3$, TMS) δ7.25–7.09 (m,3H); 5.7–5.6 (bd, 2H); 3.9 (q,1H); 3.1–1.5 (m, 14 H); 0.93 (t, J=Hz, 3H).

The (–)-enantiomer was prepared with a procedure similar to the above using A-7A as the starting material to yield as a white solid (cis-(–)-2,3,3a,4,5,9b-hexahydro-9-carboxamido-3-(n-propyl)-1H-benz[e]indole) which was recrystailized as the free base from acetone (mp 164°–165° C.) $[\alpha]_D = -240.9°$(c 0.43, CHCl$_3$). The 1HNMR (CDCl$_3$, TMS) is identical with A-8 above.

The (+)-enantiomer was prepared with a procedure similar to the above using A-7B as the starting material to yield (cis-(+)-2,3,3a,4,5,9b-hexahydro-9-carboxamido-3-(n-propyl)-1H-benz[e]indole) which was recrystallized as the free base from acetone as a white solid (mp163°–164° C.)$[\alpha]_D = +235.60°$ (c 0.815, CHCl$_3$). The 1HNMR (CDCl$_3$, TMS) is identical with A-8 above.

EXAMPLE 2 trans-(±)-1,2,3,4,4a,5,6,10b-octahydro-10-carboxamido-4-(n-propyl)-benzo[f]quinoline (B-11, Chart B)

A mixture of trans-1,2,3,4,4a,5,6,10b-octahydro-10-carboxamido-benzo[f]quinoline (B-10, 0.46 g, 2.0 mmol), 1-bromopropane (0.99 g, 8.0 mmol), and potassium carbonate (0.55 g, 4.0 mmol) in acetonitrile (40 mls) was stirred at reflux for 6 hours. The mixture was diluted with diethylether and washed with water. The aqueous was back extracted with diethylether, and the combined extracts were washed with brine, and dried (MgSO$_4$). The solvent was removed under vacuum to leave a solid (0.48 g). Crystallization from acetonitrile gave the (–) enantiomer of the title compound as an off-white solid (0.31 g, m.p. 200°–202° C., $[\alpha]_D = -287.1°$).

The (+)-enantiomer was prepared with a procedure similar to the above using (+) B-10. (m.p. 202.5°–203.5° C.,$[\alpha]_D = +294.4°$).

The racemic title compound was prepared with a procedure similar to the above using racemic B-10 to yield racemic B-11. (m.p. 207°–209°).

EXAMPLE 3 cis-(±)-2,3,3a,4,5,9b-hexahydro-9-carboxamido-1-methyl-3-(n-propyl)-1H-benz[e]indole (E-4, Chart E)

Compound E-2 (R$_1$=methyl) was carried through the sequence of reactions described in steps 3–7 of Chart C to ultimately provide E-4 (R$_1$=methyl, R=propyl); mp 172°–174° C.; 1H NMR (CDCl$_3$) δ7.29 (d, J=7.1 Hz, 1H), 7.21 (d, J=7.1 Hz, 1H), 7.11 (t, J= 7.1 Hz, 1H), 6.13 (br s, 1H), 5.92 (br s, 1H), 3.79 (t, J= 9.5 Hz, 1H), 3.11 (dd, J=10.2, 6.9 Hz, 1H), 2.99 (dd, J=10.1, 4.5 Hz, 1H), 2.88 (dt, J=12, 1.8 Hz, 1H), 2.74–2.62 (m, 1H), 2.49 (br d, J=14.1 Hz, 1H), 2.37–2.26 (m, 1H), 1.98–1.88 (m, 2H), 1.84–1.68 (m, 1H), 1.62–1.42 (m, 2H), 1.32 (tt, J=14.1, 1.7 Hz, 1H), 1.01 (d, J=6.4 Hz, 3H), 0.93 (t, J=6.5 Hz, 3H).

EXAMPLE 4 cis-(±)-2,3,3a,4,5,9b-hexahydro-3a-allyl-9-carboxamido-3-(n-propyl)-1H-benz[e]indole (E-5, Chart E)

A solution of E-3 (R$_1$=allyl, 28.02 g, 65.7 mmol) in DMSO (220 mL) was treated with powdered KOH (17.35 g, 263 mmol) and stirred at RT for 16 hours. The reaction mixture was then poured into water (1 L) and extracted with ethyl acetate (3×1.2 L). The combined organics were washed once with brine, dried over MgSO$_4$, filtered, and concentrated to a residue, from which was deposited 13.32 g of on off-white solid. An additional 8.64 g could be obtained from the mother liquor, giving a total yield of the ene-amide of 21.96 g (82%). A portion of this material (19.73 g, 48.3 mmol) was dissolved in THF (480 mL) and treated with aqueous HCl (48 mL of a 5% solution) and the mixture was heated to reflux for 8 hours. The cooled reaction mixture was concentrated, diluted with water (750 mL) and extracted with CH$_2$Cl$_2$(2×1 L). The combined organics were washed once with brine, dried over MgSO$_4$, filtered, and concentrated to a residue, from which was deposited 12.04 g of pale yellow crystals. An additional 1.76 g could be obtained from the mother liquor, giving a total yield of the amide of 13.80 g (93%). A portion of this material (11.64 g, 38 mmol) was dissolved in THF (100 mL) and added to a solution of alane (114 mmol, prepared from 114 mL of 1M LAH in THF and 15.20 g of AlCl$_3$) in THF (240 mL) at 0° C. The reaction was heated to reflux for 2 hours, cooled to RT, and treated sequentially with water (4.3 mL), 5N NaOH (3.9 mL), and water (15.1 mL). Methylene chloride (1.2 L) was added and the resulting mixture was filtered, washed with brine, dried over MgSO$_4$, filtered, and concentrated to a residue. This residue was dissolved in ether (200 mL) and treated with gaseous HCl to provide 7.27 g of a white solid. An additional 1.2 g could be obtained from the mother liquor, giving a total yield of the secondary amine of 8.44 g (68%). This material was subjected to the procedures described by steps 6 and 7 of Chart C to provide E-5 (R$_1$=allyl, R=propyl); 1H NMR (CDCl$_3$) δ 7.26–7.07 (m, 3H), 5.93 (br s, 1H), 5.88–5.72 (m, 1H), 5.71 (br s, 1H), 5.02–4.96 (m, 2H), 3.63 (t, J=7.3 Hz, 1H), 3.01–2.87 (m, 1H), 2.82 (dt, J=7.4, 1.8 Hz, 1H), 2.74–2.63 (m, 1H), 2.59–2.45 (m, 3H), 2.44–2.33 (m, 1H), 2.27 (dd, J=10.5, 7.8 Hz, 1H), 2.15 (dd, J=10.5, 7.8 Hz, 1H), 1.81–1.71 (m, H), 1.57–1.34 (m, 4H), 0.92 (t, J=7.1 Hz, 3H).

The compound cis-(–)-2,3,3a,4,5,9b-hexahydro-9-carboxamido-3-(n-propyl)-1H-benz[e]indole and its utility as an antidepressant and anxiolytic represents the best mode of practicing this invention.

We claim:

1. A compound having the Formula

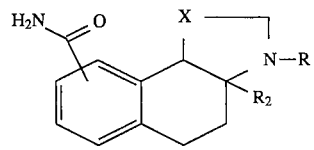

I wherein X is —(CH$_2$)$_n$— or —C(R$_1$)(H)—; R is C$_1$–C$_8$ alkyl; R$_1$ and R$_2$ are the same or different and are selected from the group consisting of hydrogen, C$_1$–C$_8$ alkyl, C$_2$–C$_8$ alkenyl, C$_2$–C$_8$ alkynyl, aryl and benzyl; and n is 1 or 2; and pharmaceutically acid addition salts thereof.

2. A compound of claim 1 having the formula

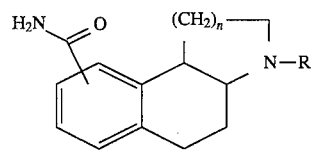

Ia wherein R is C$_1$–C$_8$ alkyl and n is 1 or 2.

3. A compound of claim 2 having the formula

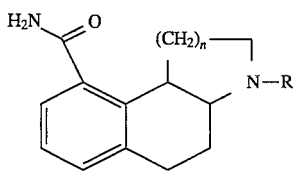

wherein R is $C_1$–$C_8$ alkyl and n is 1 or 2.

4. A compound of claim 3, wherein n is 1.

5. A compound of claim 4, cis-(±)-2,3,3a,4,5,9b-hexahydro-9-carboxamido-3-(n-propyl)-1H-benz[e]indole.

6. A compound of claim 4, cis-(+)-2,3,3a,4,5,9b-hexahydro-9-carboxamido-3-(n-propyl)-1H-benz[e]indole.

7. A compound of claim 4, cis-(−)-2,3,3a,4,5,9b-hexahydro-9-carboxamido-3-(n-propyl)-1H-benz[e]indole.

8. A compound of claim 3 wherein n is 2.

9. A compound of claim 8, trans-(±)-1,2,3,4,4a,5,6,10b-octahydro-10-carboxamido-4-(n-propyl)-benzo[f]quinoline.

10. A compound of claim 8, trans-(+)-1,2,3,4,4a,5,6,10b-octahydro-10-carboxamido-4-(n-propyl)-benzo[f]quinoline.

11. A compound of claim 8, trans-(−)-1,2,3,4,4a,5,6,10b-octahydro-10-carboxamido-4-(n-propyl)-benzo[f]quinoline.

12. A compound of claim 1 having the formula

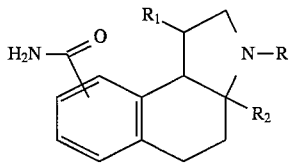

wherein one of $R_1$ and $R_2$ is always other than hydrogen and R is the same as in claim 1.

13. A compound of claim 12, cis-(±)-2,3,3a,4,5,9b-hexahydro-9-carboxamido-1-methyl-3-(n-propyl)-1H-benz[e]indole.

14. A compound of claim 12, cis-(±)-2,3,3a,4,5,9b-hexahydro-1-benzyl-9-carboxamido-3-(n-propyl)-1H-benz[e]indole.

15. A compound of claim 12, cis-(±)-2,3,3a,4,5,9b-hexahydro-3a-allyl-9carboxamido-3-(n-propyl)-1H-benz[e]indole.

16. A compound having the formula

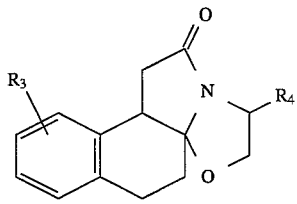

wherein $R_3$ is hydrogen, halogen, $C_1C_8$ alkyl and $C_1$–$C_8$ alkoxy; and $R_4$ is phenyl or $C_1$–$C_8$ alkyl or benzyl.

17. A compound of claim 16 wherein $R_3$ is halogen.

18. A compound of claim 17, [4bS-(4b.alpha., 8.beta., 10aR*)]-4-bromo-4b,5,8,9,11,12-hexahydro-8-phenyl-6H-Benz[e]oxazolo[2,3-i]indol-6-one.

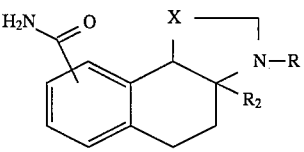

* * * * *